United States Patent
Kuramoto

(10) Patent No.: US 10,186,033 B2
(45) Date of Patent: Jan. 22, 2019

(54) MEDICAL IMAGE PROCESSING DEVICE, OPERATION METHOD THEREFOR, AND ENDOSCOPE SYSTEM

(71) Applicant: FUJIFILM Corporation, Tokyo (JP)

(72) Inventor: Masayuki Kuramoto, Ashigarakami-gun (JP)

(73) Assignee: FUJIFILM Corporation, tokyo (JP)

( * ) Notice: Subject to any disclaimer, the term of this patent is extended or adjusted under 35 U.S.C. 154(b) by 0 days.

(21) Appl. No.: 15/864,324

(22) Filed: Jan. 8, 2018

(65) Prior Publication Data

US 2018/0130208 A1 May 10, 2018

Related U.S. Application Data

(60) Division of application No. 15/279,541, filed on Sep. 29, 2016, now Pat. No. 9,892,512, which is a
(Continued)

(30) Foreign Application Priority Data

Mar. 31, 2014 (JP) .................. 2014-074273
Jun. 27, 2014 (JP) .................. 2014-133388

(51) Int. Cl.
*G06K 9/00* (2006.01)
*G06T 7/00* (2017.01)
(Continued)

(52) U.S. Cl.
CPC ........ *G06T 7/0014* (2013.01); *A61B 1/00009* (2013.01); *A61B 1/041* (2013.01);
(Continued)

(58) Field of Classification Search
None
See application file for complete search history.

(56) References Cited

U.S. PATENT DOCUMENTS

| | | |
|---|---|---|
| 4,860,091 A | 8/1989 | Kimura et al. |
| 5,550,582 A | 8/1996 | Takasugi et al. |
| | (Continued) | |

FOREIGN PATENT DOCUMENTS

JP  2007-307395 A  11/2007

OTHER PUBLICATIONS

Chinese Office Action, dated Aug. 23, 2017, for Chinese Application No. 201580018139.1, along with an English translation.
(Continued)

*Primary Examiner* — Nancy Bitar
(74) *Attorney, Agent, or Firm* — Birch, Stewart, Kolasch & Birch, LLP

(57) ABSTRACT

Disclosed is a medical image processing device for generating an image in which a difference in color between an abnormal part where a gastric mucosa is atrophied, and a normal part is enhanced.
A B/G ratio is determined from B and G image signals, and a G/R ratio is determined from the G and R image signals. In a feature space formed from the B/G ratio and the G/R ratio, first processing is performed for moving the coordinates of a second range to a reference range including the origin in a state where the coordinates of first and third ranges are maintained. In order to make the first range and the third range distant from each other, second processing is performed for moving the first and third ranges. A first special image is generated based on the B/G ratio and the G/R ratio after the first and second processing.

13 Claims, 19 Drawing Sheets

Related U.S. Application Data continuation of application No. PCT/JP2015/055537, filed on Feb. 26, 2015.

(51) Int. Cl.

| | | |
|---|---|---|
| *G02B 23/24* | (2006.01) | |
| *A61B 1/00* | (2006.01) | |
| *G06T 7/11* | (2017.01) | |
| *G06T 7/90* | (2017.01) | |
| *A61B 1/04* | (2006.01) | |
| *A61B 5/00* | (2006.01) | |
| *G06K 9/46* | (2006.01) | |
| *G06K 9/62* | (2006.01) | |
| *H04N 5/232* | (2006.01) | |
| *A61B 5/103* | (2006.01) | |
| *A61B 5/07* | (2006.01) | |
| *H04N 5/225* | (2006.01) | |

(52) U.S. Cl.
CPC ............ *A61B 5/073* (2013.01); *A61B 5/1032* (2013.01); *A61B 5/4222* (2013.01); *A61B 5/4238* (2013.01); *G02B 23/24* (2013.01); *G06K 9/4652* (2013.01); *G06K 9/6203* (2013.01); *G06T 7/0012* (2013.01); *G06T 7/11* (2017.01); *G06T 7/90* (2017.01); *H04N 5/23293* (2013.01); *A61B 2576/02* (2013.01); *G06T 2207/10068* (2013.01); *G06T 2207/30096* (2013.01); *G06T 2207/30101* (2013.01); *H04N 2005/2255* (2013.01)

(56) References Cited

U.S. PATENT DOCUMENTS

| | | | |
|---|---|---|---|
| 5,675,378 A | 10/1997 | Takasugi et al. | |
| 9,582,878 B2 | 2/2017 | Kuramoto | |
| 9,582,900 B2 * | 2/2017 | Moriya | G06T 7/0012 |
| 9,977,232 B2 * | 5/2018 | Otani | G02B 23/2461 |
| 2004/0225223 A1 | 11/2004 | Honda et al. | |
| 2009/0027413 A1 | 1/2009 | Pyo | |
| 2009/0270702 A1 * | 10/2009 | Zeng | A61B 5/0075 600/323 |
| 2011/0237884 A1 * | 9/2011 | Saito | A61B 1/00009 600/109 |
| 2012/0116192 A1 * | 5/2012 | Saito | A61B 1/00009 600/323 |
| 2012/0154567 A1 * | 6/2012 | Yamaguchi | A61B 1/0638 348/68 |
| 2012/0253122 A1 | 10/2012 | Minetoma et al. | |
| 2014/0333655 A1 | 11/2014 | Tu | |
| 2015/0269750 A1 | 9/2015 | Moriya | |
| 2016/0223807 A1 * | 8/2016 | Otani | G02B 23/2461 |

OTHER PUBLICATIONS

Extended European Search Report issued in European Application No. 15773911.1 dated Mar. 14, 2017.

International Search Report for PCT/JP2015/055537 dated May 26, 2015.

Written Opinion of the International Searching Authority for PCT/JP2015/055537 dated May 26, 2015.

* cited by examiner (A)　　FIRST PROCESSING　　(B)

REFERENCE RANGE (A)    (B)

MEDICAL IMAGE PROCESSING DEVICE, OPERATION METHOD THEREFOR, AND ENDOSCOPE SYSTEM

CROSS-REFERENCE TO RELATED APPLICATION

This application is a Divisional of co-pending U.S. patent application Ser. No. 15/279,541, filed Sep. 29, 2016, which is a continuation of PCT Application PCT/JP2015/055537 filed on Feb. 26, 2015, which claims priority under 35 USC 119(a) from Japanese Patent Application No. 2014-074273 filed on Mar. 31, 2014, and Japanese Patent Application No. 2014-133388 filed on Jun. 27, 2014. The above applications are hereby expressly incorporated by reference, in their entirety, into the present application.

BACKGROUND OF THE INVENTION

1. Field of the Invention

The present invention relates to a medical image processing device for generating an image in which the difference in color between a normal part and a lesion part is enhanced, an operation method therefor, and an endoscope system.

2. Description of the Related Art

In a medical field, diagnosis using an endoscope system comprising a light source device, an endoscope, and a processor device has been widely performed. In this endoscope system, an observation target is irradiated with illumination light from the endoscope, and an image of the observation target is displayed on a monitor based on an image signal obtained by imaging the observation target being irradiated with illumination light with an imaging element of the endoscope. A doctor detects the presence or absence of a lesion part while viewing the image displayed on the monitor.

It is possible to easily detect a lesion part, such as a lesion part significantly protruding from a mucosal surface, which is significantly different in shape or size from a normal part. However, a lesion part which is nearly the same in shape or size as a normal part is detected based on a difference in color from the normal part. In this case, it is extremely difficult to detect a lesion part in a case where the lesion part has not progressed and the color thereof is nearly the same as that of the normal part.

Accordingly, in JP3228627B (corresponding to U.S. Pat. No. 5,550,582 and U.S. Pat. No. 5,675,378), the difference in color between a normal part and a lesion part is made distinct by processing a part where a value of a blood volume (hemoglobin index) is distant from a reference value such that the value of the blood volume becomes more distant from the reference value.

It is known that, in a case of a gastric cancer among the lesion parts, a gastric mucosa is atrophied and the gastric mucosa is faded. For this reason, an atrophic part where atrophy occurs in a mucosa is different in color from a normal part where atrophy does not occur. The presence or absence of a gastric cancer is diagnosed by observing the difference in color from the normal part with the endoscope (there is an ABC examination which is recommended by Certified NPO: Japan Research Foundation of Prediction, Diagnosis and Therapy for Gastric Cancer).

In a case where atrophy has progressed to a high degree (for example, in a case where atrophy is included in a group C or a group D in the ABC examination), since the difference in color between a normal part and an atrophic part is distinct, it is possible to easily detect the atrophic part. However, in a case where atrophy is progressing (for example, in a case where atrophy is included in a group B or a group C in the ABC examination), since the difference in color between an atrophic part and a normal part is slight, it is difficult to detect an atrophic part only with the difference in color. Accordingly, there is demand for easy detection of an atrophic part by enhancing the difference in color between a normal part and an atrophic part even in a case where the difference in color between an atrophic part and a normal part is slight as when in the event that atrophy is progressing.

It is considered that the difference in color between an atrophic part and a normal part is enhanced by the method of JP3228627B. However, since the color of the atrophic part is affected by not only the blood volume but also elements other than the blood volume, in the method of JP3228627B, it is difficult to enhance the difference in color between an atrophic part and a normal part.

SUMMARY OF THE INVENTION

An object of the invention is to provide a medical image processing device for generating an image in which the difference in color between an abnormal part, such as an atrophic part where a gastric mucosa is atrophied, and a normal part is enhanced, an operation method therefor, and an endoscope system.

A medical image processing device of the invention comprises an image signal input processing unit which performs input processing of a first color image signal, a signal ratio calculation unit which calculates a first signal ratio between image signals of two colors in the first color image signal and a second signal ratio between image signals of two colors different from those in the first signal ratio, and a first moving processing unit which performs, in a feature space formed by the first signal ratio and the second signal ratio, first processing for moving, among a first range, a second range, and a third range where an observation target in a subject is distributed, the coordinates of the second range to a reference range determined in the feature space, and second processing for moving at least one of the coordinates of the first range and the coordinates of the third range without moving the second range.

It is preferable that the first processing is performed for moving the coordinates of the second range to the reference range by changing a radius vector of the coordinates of the second range in the feature space. It is preferable that the second processing is performed for moving the coordinates of the first range and the coordinates of the third range so as to be distant from each other by changing an angle of the coordinates of the first range and an angle of the coordinates of the third range in the feature space. It is preferable that the reference range is a range which includes the origin of the feature space, and does not include the first range and the third range.

It is preferable that medical image processing device further comprises a second moving processing unit which performs, in the feature space, first processing for moving the coordinates of the second range to a reference range determined in the feature space, and in the feature space, third processing for moving the third range in a state where the coordinates of the first range are maintained. It is preferable that the third processing is performed for moving the coordinates of the third range such that the hue of a second special image obtained from the first signal ratio and the second signal ratio after the first and third processing is changed.

It is preferable that the medical image processing device further comprises a color image signal conversion unit which converts the first signal ratio and the second signal ratio after the first and second processing to a second color image signal or converts the first signal ratio and the second signal ratio after the first and third processing to a second color image signal, and a brightness adjustment unit which adjusts the pixel values of the second color image signal from first brightness information obtained from the first color image signal and second brightness information obtained from the second color image signal.

It is preferable that, in the feature space, the difference between the first range and the second range in a case where the image signal of at least one color of the first color image signal is a narrowband signal is greater than the difference between the first range and the second range in a case where the image signals of all colors of the first color image signal are broadband signals, or the difference between the first range and the third range in a case where the image signal of at least one color of the first color image signal is a narrowband signal is greater than the difference between the first range and the third range in a case where the image signals of all colors of the first color image signal are broadband signals.

It is preferable that the first signal ratio correlates with a blood vessel depth and the second signal ratio correlates with a blood volume. It is preferable that the first signal ratio is a B/G ratio and the second signal ratio is a G/R ratio.

An endoscope system of the invention comprises the medical image processing device of the invention described above, and a display unit which displays a first special image obtained from the first signal ratio and the second signal ratio after the first and second processing and a second special image obtained from the first signal ratio and the second signal ratio after the first and third processing.

An operation method for a medical image processing device of the invention comprises a step in which an image signal input processing unit performs input processing of a first color image signal, a step in which a signal ratio calculation unit calculates a first signal ratio between image signals of two colors in the first color image signal and a second signal ratio between image signals of two colors different from those in the first signal ratio, and a step in which a first moving processing unit performs, in a feature space formed by the first signal ratio and the second signal ratio, first processing for moving, among a first range, a second range, and a third range where an observation target in a subject is distributed, the coordinates of the second range to a reference range determined in the feature space, and second processing for moving at least one of the coordinates of the first range and the coordinates of the third range without moving the second range.

According to the invention, it is possible to generate an image in which the difference in color between an abnormal part, such as an atrophic part where a gastric mucosa is atrophied, and a normal part is enhanced.

DESCRIPTION OF THE PREFERRED EMBODIMENTS

First Embodiment

Figure 1:
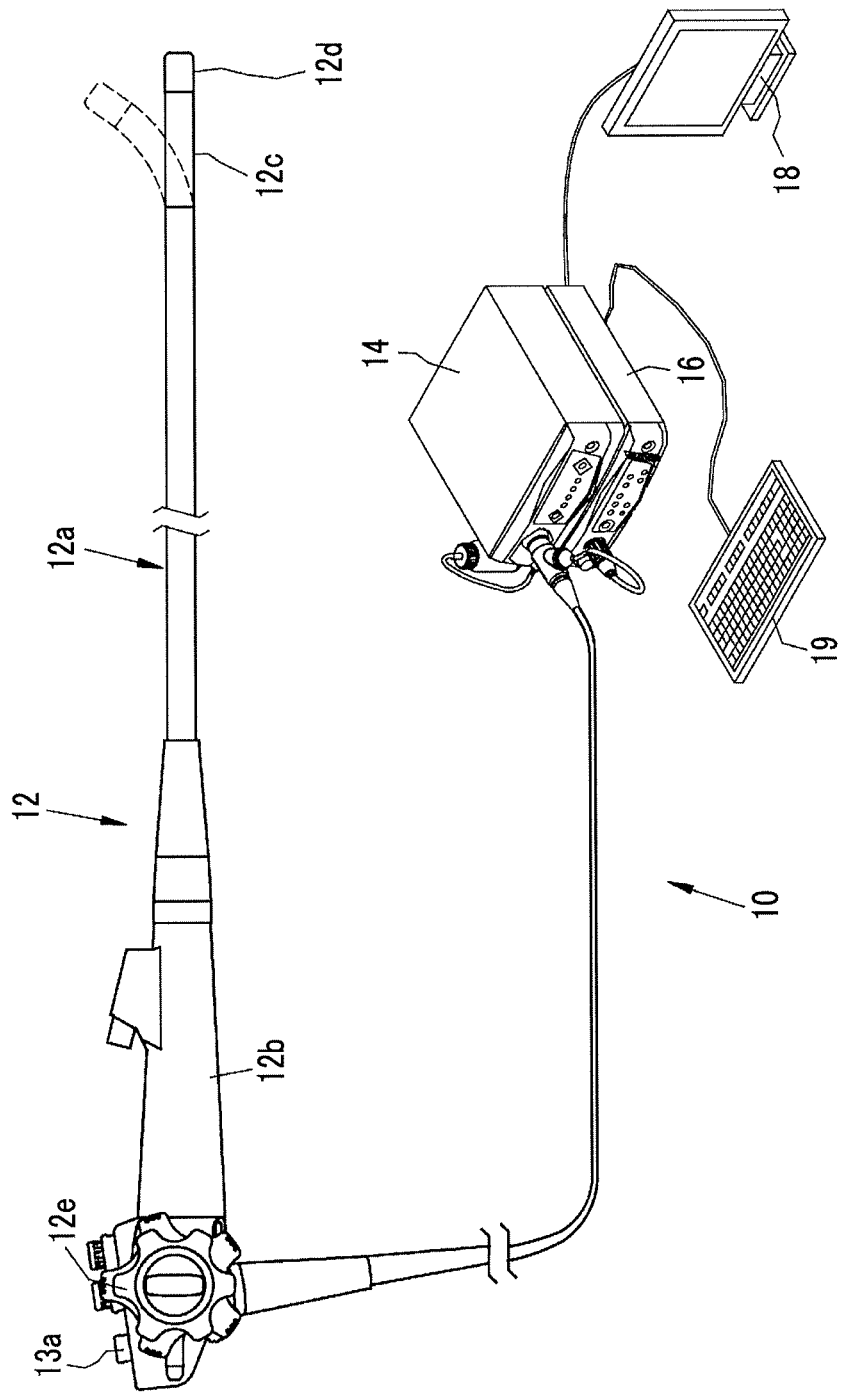
FIG. 1 is an appearance diagram of an endoscope system of a first embodiment.

As shown in FIG. 1, an endoscope system 10 of a first embodiment has an endoscope 12, a light source device 14, a processor device 16, a monitor 18 (display unit), and a console 19. The endoscope 12 is optically connected to the light source device 14 and electrically connected to the processor device 16. The endoscope 12 has an insertion portion 12a which is inserted into a subject, an operation portion 12b which is provided in a base portion of the insertion portion 12a, and a bending portion 12c and a tip portion 12d which are provided on the tip side of the insertion portion 12a. The bending portion 12c is bent by operating an angle knob 12e of the operation portion 12b. The tip portion 12d is directed in a desired direction with this bending operation.

The operation portion 12b is provided with a mode selection SW 13a, in addition to the angle knob 12e. The mode selection SW 13a is used for a switching operation between four modes of a normal observation mode, a first special observation mode, a second special observation mode, and a simultaneous observation mode. The normal observation mode is a mode in which a normal image is displayed on the monitor 18. The first special observation mode is a mode which is used in order to observe the boundary between an atrophic part where atrophy occurs in a gastric mucosa due to a lesion, such as a gastric cancer, and a normal part and in which a first special image is displayed on the monitor 18. The second special observation mode is a mode which is used in order to observe the difference in color between an atrophic part and a normal part and in which a second special image is displayed on the monitor 18. The simultaneous observation mode is a mode which is used in order to simultaneously observe the boundary between an atrophic part and a normal part and the difference in color between the atrophic part and the normal part and in which a first special image and a second special image are displayed on the monitor 18 simultaneously.

The processor device 16 is electrically connected to the monitor 18 and the console 19. The monitor 18 outputs and displays image information or the like. The console 19 functions as a user interface (UI) which receives an input operation, such as function setting. An external recording unit (not shown) which records image information or the like may be connected to the processor device 16.

Figure 2:
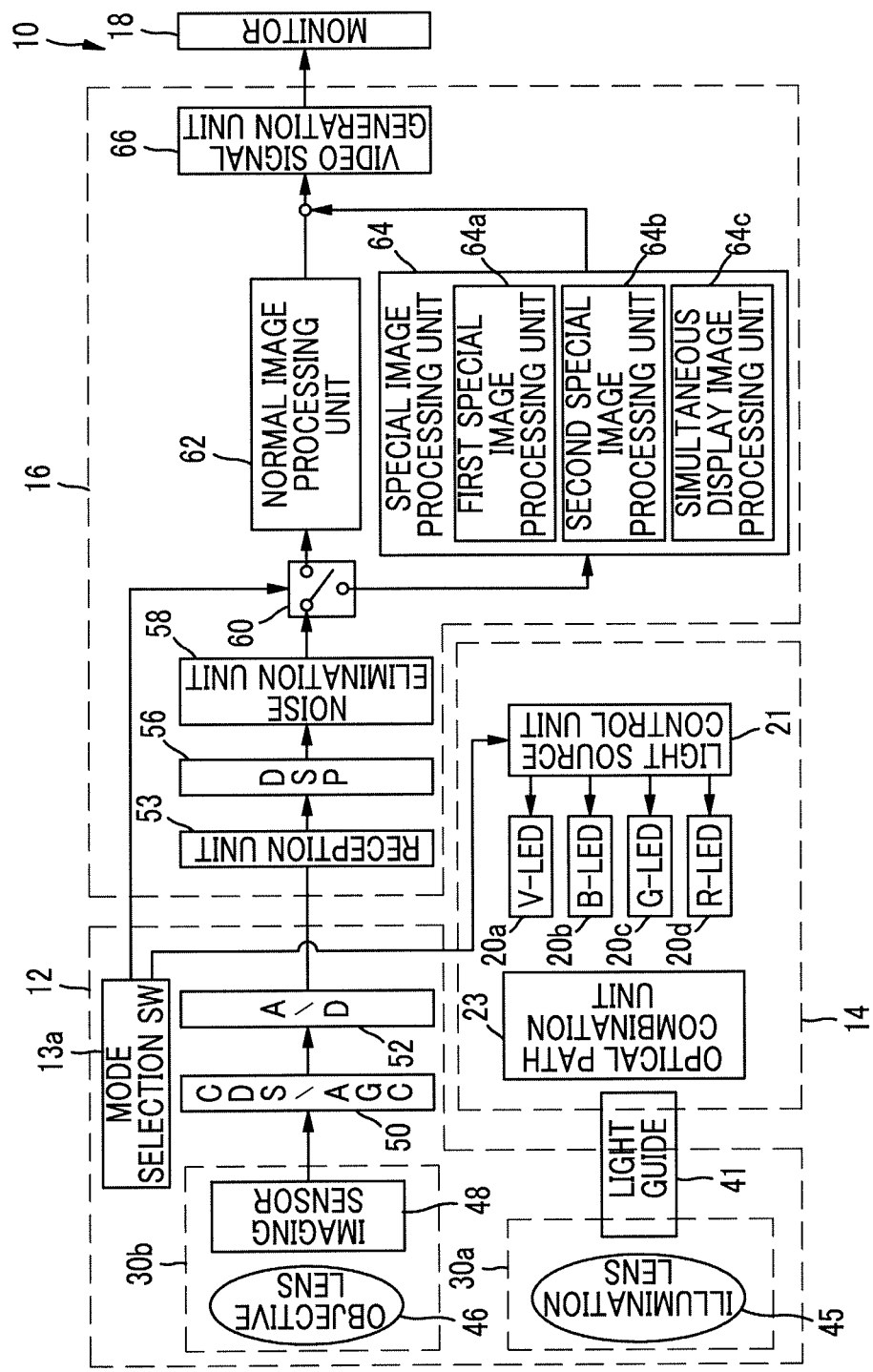
FIG. 2 is a block diagram showing functions of the endoscope system of the first embodiment.

As shown in FIG. 2, the light source device 14 comprises a violet light emitting diode (V-LED) 20a, a blue light emitting diode (B-LED) 20b, a green light emitting diode (G-LED) 20c, a red light emitting diode (R-LED) 20d, a light source control unit 21 which controls driving of the LEDs 20a to 20d of the four colors, and an optical path combination unit 23 which combines the optical paths of light of four colors emitted from the LEDs 20a to 20d of the four colors. The inside of the subject is irradiated with light coupled by the optical path combination unit 23 through a light guide 41 and an illumination lens 45 inserted into the insertion portion 12a. A laser diode (LD) may be used instead of the LED.

Figure 3:
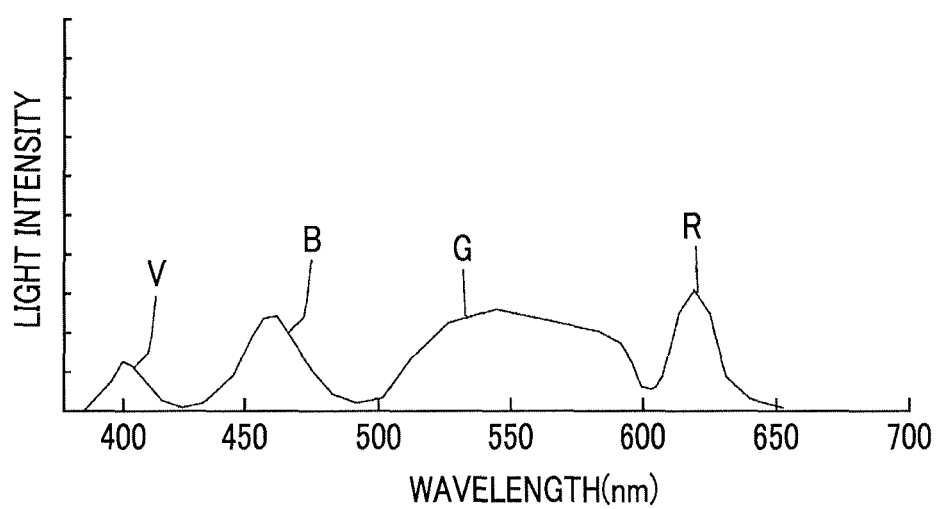
FIG. 3 is a graph showing light emission spectra of violet light V, blue light B, green light G, and red light R.

As shown in FIG. 3, the V-LED 20a generates violet light V having a center wavelength of 405±10 nm and a wavelength range of 380 nm to 420 nm. The B-LED 20b generates blue light B having a center wavelength of 460±10 nm and a wavelength range of 420 nm to 500 nm. The G-LED 20c generates green light G having a wavelength range of 480 nm to 600 nm. The R-LED 20d generates red light R having a center wavelength of 620 nm to 630 nm and a wavelength range of 600 nm to 650 nm. In each of the LEDs 20a to 20d, the center wavelength may be the same as or different from the peak wavelength.

The light source control unit 21 turns on the V-LED 20a, the B-LED 20b, the G-LED 20c, and the R-LED 20d in any observation mode of the normal observation mode, the first special observation mode, the second special observation mode, and the simultaneous observation mode. Accordingly, an observation target is irradiated with mixed light of light of the four colors of violet light V, blue light B, green light G, and red light R. In the normal observation mode, the light source control unit 21 controls the LEDs 20a to 20d such that a light quantity ratio among violet light V, blue light B, green light G, and red light R becomes Vc:Bc:Gc:Rc. In the first special observation mode, the second special observation mode, and the simultaneous observation mode, the light source control unit 21 controls the LEDs 20a to 20d such that the light quantity ratio among violet light V, blue light B, green light G, and red light R becomes Vs:Bs:Gs:Rs.

As shown in FIG. 2, the light guide 41 is embedded in the endoscope 12 and a universal cord (a cord connecting the endoscope 12, the light source device 14, and the processor device 16), and light combined by the optical path combination unit 23 propagates to the tip portion 12d of the endoscope 12. As the light guide 41, a multi-mode fiber is available. As an example, a slender fiber cable which has a core diameter of 105 µm, a clad diameter of 125 µm, and a diameter of 0.3 to 0.5 mm including a protective layer as a sheath is available.

The tip portion 12d of the endoscope 12 is provided with an illumination optical system 30a and an imaging optical system 30b. The illumination optical system 30a has an illumination lens 45, and the observation target is irradiated with light from the light guide 41 through the illumination lens 45. The imaging optical system 30b has an objective lens 46 and an imaging sensor 48. Reflected light from the observation target is incident on the imaging sensor 48 through the objective lens 46. With this, a reflected image of the observation target is formed on the imaging sensor 48.

The imaging sensor 48 is a color imaging sensor, captures a reflected image of the subject, and output an image signal. It is preferable that the imaging sensor 48 is a charge coupled device (CCD) imaging sensor, a complementary metal-oxide semiconductor (CMOS) imaging sensor, or the like. The imaging sensor 48 used in the invention is a color imaging sensor for obtaining RGB image signals of three colors of red (R), green (G), and blue (B), that is, a so-called RGB imaging sensor comprising R pixels with R filters, G pixels with G filters, and B pixels with B filters.

The imaging sensor 48 may be a so-called complementary color imaging sensor comprising complementary color filters of cyan (C), magenta (M), yellow (Y), and green (G), instead of the RGB color imaging sensor. In a case where the complementary color imaging sensor is used, since image signals of four colors of CMYG are output, it is necessary to convert the image signals of the four colors of CMYG to image signals of three colors of RGB through complementary color/primary color conversion. The imaging sensor 48 may be a monochrome imaging sensor with no color filters. In this case, it is necessary that the light source control unit 21 turns on blue light B, green light G, and red light R in a time-division manner, and it is necessary also to synchronize processing of captured signals.

The image signals output from the imaging sensor 48 are transmitted to a CDS/AGC circuit 50. The CDS/AGC circuit 50 performs correlated double sampling (CDS) or automatic gain control (AGC) on the image signals as analog signals. The image signals having passed through the CDS/AGC circuit 50 are converted to digital image signals by an analog/digital (A/D) converter 52. The A/D-converted digital image signals are input to the processor device 16.

The processor device 16 comprises a reception unit 53, a digital signal processor (DSP) 56, a noise elimination unit 58, an image processing switching unit 60, a normal image processing unit 62, a special image processing unit 64, and a video signal generation unit 66. The reception unit 53 receives digital RGB image signals from the endoscope 12. The R image signal corresponds to signals output from the R pixels of the imaging sensor 48, the G image signal corresponds to signals output from the G pixels of the imaging sensor 48, and the B image signal corresponds to signals output from the B pixels of the imaging sensor 48.

The DSP 56 subjects the received image signals to various kinds of signal processing, such as defect correction processing, offset processing, gain correction processing, linear matrix processing, gamma conversion processing, and demosaic processing. In the defect correction processing, signals from defective pixels of the imaging sensor 48 are corrected. In the offset processing, dark current components are removed from the RGB image signals subjected to the defect correction processing, and an accurate zero level is set. In the gain correction processing, a signal level is adjusted by multiplying the RGB image signals after the offset processing by a specific gain. The RGB image signals after the gain correction processing are subjected to the linear matrix processing for increasing color reproducibility. Thereafter, brightness or saturation is adjusted by the gamma conversion processing. The RGB image signals after the linear matrix processing are subjected to the demosaic processing (also referred to as equalization processing or synchronization processing), and signals of colors lacking in each pixel are generated by interpolation. With the demosaic processing, all pixels have signals of the respective colors of RGB.

The noise elimination unit 58 performs noise elimination processing (for example, a moving average method, a median filter method, or the like) on the RGB image signals subjected to gamma correction or the like in the DSP 56 to eliminate noise from the RGB image signals. The noise-eliminated RGB image signals are transmitted to the image processing switching unit 60. An "image signal input processing unit" of the invention corresponds to a configuration including the reception unit 53, the DSP 56, and the noise elimination unit 58.

The image processing switching unit 60 transits the RGB image signals to the normal image processing unit 62 in a case where the normal observation mode is set by the mode selection SW 13a, and transmits the RGB image signals to the special image processing unit 64 in a case where the first special observation mode, the second special observation mode, or the simultaneous observation mode is set.

The normal image processing unit 62 performs color conversion processing, color enhancement processing, and structure enhancement processing on the RGB image signals. In the color conversion processing, the digital RGB image signals are subjected to 3×3 matrix processing, gradation conversion processing, three-dimensional LUT processing, or the like and are converted to RGB image signals subjected to the color conversion processing. Next, the RGB image signals subjected to the color conversion processing are subjected to various kinds of color enhancement processing. The RGB image signals subjected to the color enhancement processing are subjected to structure enhancement processing, such as spatial frequency enhancement.

The RGB image signals subjected to the structure enhancement processing are input as RGB image signals of a normal image from the normal image processing unit 62 to the video signal generation unit 66.

The special image processing unit 64 operates in a case where the first special observation mode, the second special observation mode, or the simultaneous observation mode is set. The special image processing unit 64 comprises a first special image processing unit 64a which generates a first special image, a second special image processing unit 64b which generates a second special image, and a simultaneous display image processing unit 64c which generates a special image for simultaneous display for simultaneously displaying the first special image and the second special image. However, the first special image processing unit 64a does not generate the second special image. Furthermore, the second special image processing unit 64b does not generate the first special image. The details of the first special image processing unit 64a, the second special image processing unit 64b, and the simultaneous display image processing unit 64c will be described below. The RGB image signals of the first special image, the second special image, the special image for simultaneous display generated by the special image processing unit 64 are input to the video signal generation unit 66.

The video signal generation unit 66 converts the RGB image signals input from the normal image processing unit 62 or the special image processing unit 64 to a video signal for display as an image displayable on the monitor 18. The monitor 18 displays the normal image, the first special image, or the second special image, or simultaneously displays the first special image and the second special image based on the video signal.

Figure 4:
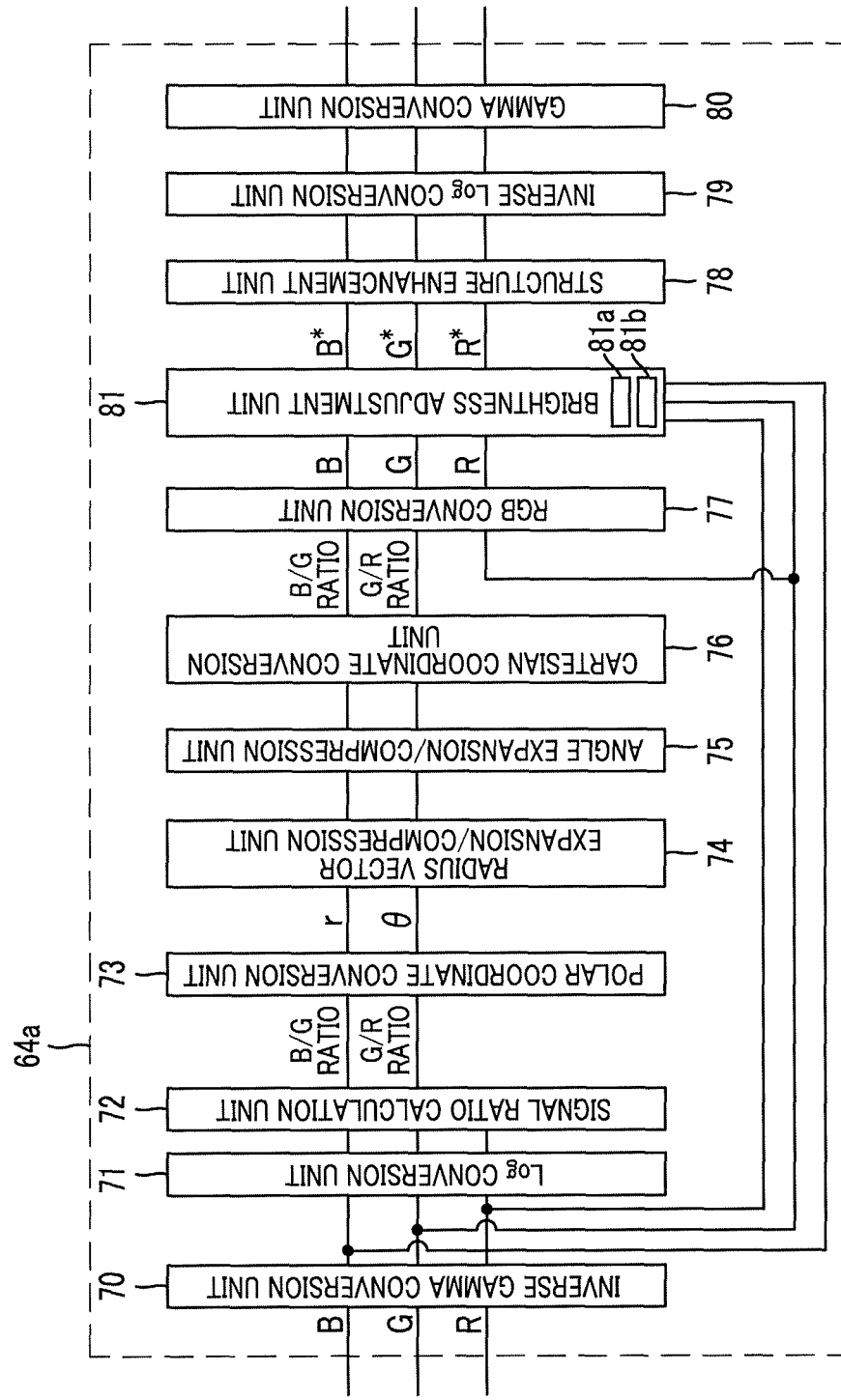
FIG. 4 is a block diagram showing functions of a first special image processing unit.

As shown in FIG. 4, the first special image processing unit 64a comprises an inverse gamma conversion unit 70, a Log conversion unit 71, a signal ratio calculation unit 72, a polar coordinate conversion unit 73, a radius vector expansion/compression unit 74, an angle expansion/compression unit 75, a Cartesian coordinate conversion unit 76, an RGB conversion unit 77, a structure enhancement unit 78, an inverse Log conversion unit 79, and a gamma conversion unit 80. The first special image processing unit 64a comprises a brightness adjustment unit 81 between the RGB conversion unit 77 and the structure enhancement unit 78. A "first moving processing unit" of the invention corresponds to a configuration including the radius vector expansion/compression unit 74 and the angle expansion/compression unit 75 in the first special image processing unit 64a.

The inverse gamma conversion unit 70 subjects the input RGB image signals to inverse gamma conversion. Since the RGB image signals after inverse gamma conversion are reflectance linear RGB signals which are linear with respect to reflectance from the specimen, the ratio of a signal associated with various kinds of biological information of the specimen among the RGB image signals becomes high. The reflectance linear R image signal is referred to as a first R image signal, the reflectance linear G image signal is referred to as a first G image signal, and the reflectance linear B image signal is referred to as a first B image signal.

The Log conversion unit 71 subjects the first RGB image signals (corresponding to a "first color image signal") to Log conversion. With this, an R image signal (log R) subjected to Log conversion, a G image signal (log G) subjected to Log conversion, and a B image signal (log B) subjected to Log conversion are obtained. The signal ratio calculation unit 72 performs difference processing (log G−log B=log G/B=−log(B/G)) based on the G image signal and the B image signal subjected to Log conversion to calculate the B/G ratio. The "B/G ratio" refers to −log(B/G) with "−log" omitted. Difference processing (log R−log G=log R/G=−log (G/R)) is performed based on the R image signal and the G image signal subjected to Log conversion to calculate the G/R ratio. Similarly to the B/G ratio, the G/R ratio refers to −log(G/R) with "−log" omitted.

The B/G ratio and the G/R ratio are determined from the pixel values of the pixels at the same positions in the B image signal, the G image signal, and the R image signal. The B/G ratio and the G/R ratio are determined for each pixel. The B/G ratio correlates with a blood vessel depth (the distance between the mucosal surface and a position of a specific blood vessel); thus, the B/G ratio varies with a difference in blood vessel depth. The G/R ratio correlates with a blood volume (hemoglobin index); thus, the G/R ratio varies with variation in blood volume.

The polar coordinate conversion unit 73 converts the B/G ratio and the G/R ratio determined by the signal ratio calculation unit 72 to a radius vector r and an angle θ. The polar coordinate conversion unit 73 performs the conversion to the radius vector r and the angle θ for all pixels. The radius vector expansion/compression unit 74 performs first processing for expanding or compressing the radius vector r based on the radius vector r and the angle θ converted by the polar coordinate conversion unit 73. The angle expansion/compression unit 75 performs second processing for expanding or compressing the angle θ based on the radius vector r subjected to the first processing in the radius vector expansion/compression unit 74 and the angle θ. The details of the first and second processing will be described below.

The Cartesian coordinate conversion unit 76 converts the angle-expanded or angle-compressed radius vector r and angle θ subjected to the second processing in the angle expansion/compression unit 75 to Cartesian coordinates. With this, the radius vector r and angle θ are converted to the B/G ratio and the G/R ratio again. The RGB conversion unit 77 (corresponding to a "color image signal conversion unit" of the invention) converts the B/G ratio and the G/R ratio having passed through the Cartesian coordinate conversion unit 76 to second RGB image signals (corresponding to a "second color image signal" of the invention) using at least one image signal among the first RGB image signals. For example, the RGB conversion unit 77 converts the B/G ratio to the second B image signal by performing arithmetic operation based on the G image signal among the first RGB image signals and the B/G ratio. The RGB conversion unit 77 converts the G/R ratio to the second R image signal by performing arithmetic operation based on the G image signal among the first RGB image signals and the G/R ratio. The RGB conversion unit 77 outputs the first G image signal as the second G image signal without performing special conversion.

The brightness adjustment unit 81 adjusts the pixel values of the second RGB image signals using the first RGB image signals and the second RGB image signals. The reason that the brightness adjustment unit 81 adjusts the pixel values of the second RGB image signals is as follows. The second RGB image signals obtained by expanding or compressing the color areas in the radius vector expansion/compression unit 74 and the angle expansion/compression unit 75 may be significantly changed in brightness from the first RGB image signals. Accordingly, the brightness adjustment unit 81 adjusts the pixel values of the second RGB image signals to make the second RGB image signals after brightness adjustment equal in brightness to the first RGB image signals.

The brightness adjustment unit 81 comprises a first brightness information calculation unit 81a which determines first brightness information Yin based on the first RGB image signals, and a second brightness information calculation unit 81b which determines second brightness information Yout based on the second RGB image signals. The first brightness information calculation unit 81a calculates the first brightness information Yin according to an arithmetic expression "kr×pixel value of first R image signal+kg×pixel value of first G image signal+kb×pixel value of first B image signal". Similarly to the first brightness information calculation unit 81a, the second brightness information calculation unit 81b calculates the second brightness information Yout according to the same arithmetic expression as described above. Assuming that the first brightness information Yin and the second brightness information Yout are determined, the brightness adjustment unit 81 adjusts the pixel values of the second RGB image signals by performing arithmetic operation based on Expressions (E1) to (E3) described below.

$R^*$=pixel value of second $R$ image signal×Yin/Yout   (E1):

$G^*$=pixel value of second $G$ image signal×Yin/Yout   (E2):

$B^*$=pixel value of second $B$ image signal×Yin/Yout   (E3):

"R*" represents the second R image signal after brightness adjustment, "G*" represents the second G image signal after brightness adjustment, and "B*" represents the second B image signal after brightness adjustment. "kr", "kg", and "kb" are arbitrary constants within a range of "0" to "1".

The structure enhancement unit 78 subjects the second RGB image signals after brightness adjustment in the brightness adjustment unit 81 to the structure enhancement processing. As the structure enhancement processing, frequency filtering or the like is used. The inverse Log conversion unit 79 subjects the second RGB image signals having passed through the structure enhancement unit 78 to inverse Log conversion. With this, the second RGB image signals having antilogarithmic pixel values. The gamma conversion unit 80 subjects the second RGB image signals having passed through the inverse Log conversion unit 79 to gamma conversion. With this, the second RGB image signals having the gradation suitable for an output device, such as the monitor 18, are obtained. The RGB image signals having passed through the gamma conversion unit 80 are sent to the simultaneous display image processing unit 64c or the video signal generation unit 66 as the RGB image signal of the first special image.

Figure 5:
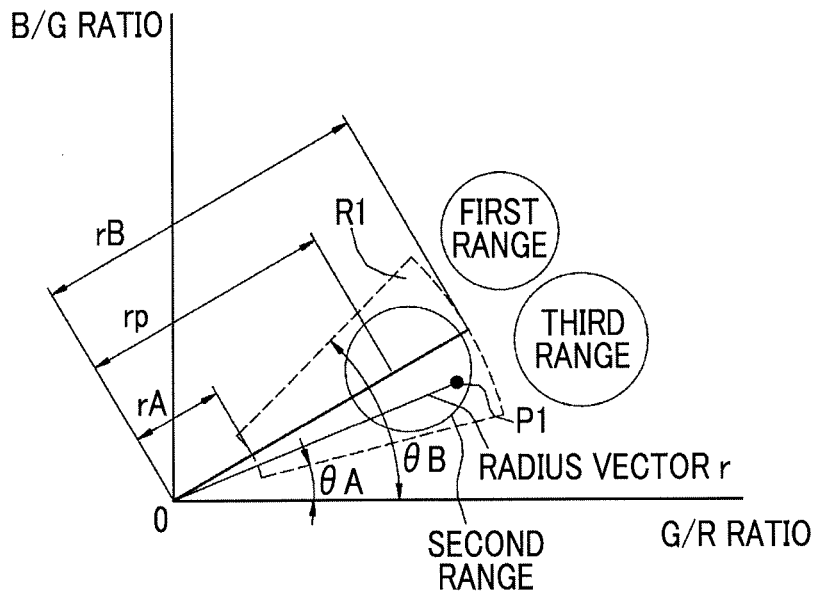
FIG. 5 is an explanatory view showing first processing.

The content of the first processing in the radius vector expansion/compression unit 74 will be described below using a feature space which is a two-dimensional color space formed by the B/G ratio on the vertical axis and the G/R ratio on the horizontal axis as shown in FIG. 5. In the first processing, in the feature space, the radius vector r of coordinates P1 within a radius vector variation range R1 is changed, and the radius vector of coordinates outside the radius vector variation range R1 is not changed. In the radius vector variation range R1, the radius vector r is within a range of "rA" to "rB", and the angle θ is within a range of "θA" to "θB" (rA<rB, θA<θB). The radius vector variation range R1 is an area including a second range in which an atrophic mucosa atrophied due to atrophic gastritis is distributed, and is set so as not to include a first range in which a normal mucosa is distributed and a third range which is below the atrophic mucosa atrophied due to atrophic gastritis and in which a deep blood vessel which becomes see-through along with atrophy is distributed.

Figure 6:
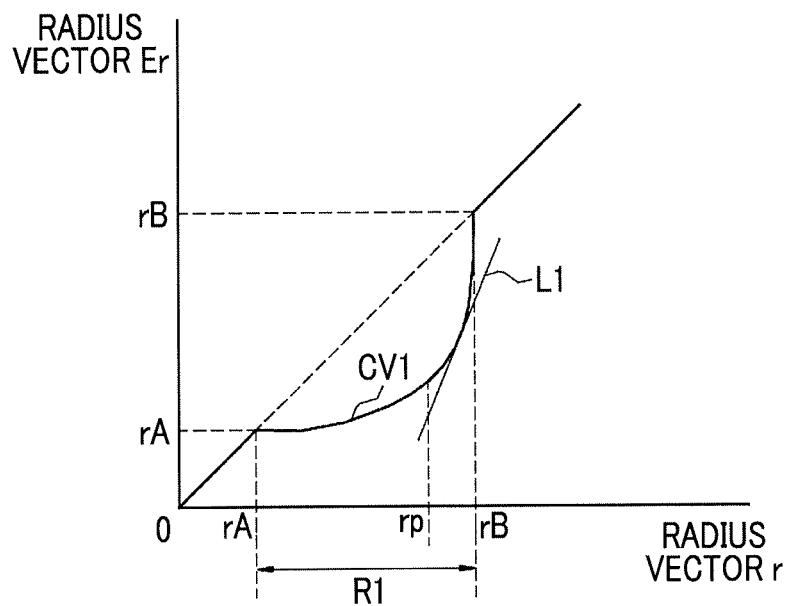
FIG. 6 is a graph showing the relationship between a radius vector r and a radius vector Er.

As shown in FIG. 6, in the first processing, in the event that the radius vector r is within a range of "rp" to "rB", expansion processing for changing the radius vector r at a radius vector change rate Vx greater than "1" is performed, and in the event that the radius vector r is within a range of "rA" to "rp", compression processing for changing the radius vector r at a radius vector change rate Vy smaller than "1" is performed. With the expansion processing and the compression processing, the radius vector r within the radius vector variation range R1 is changed to the radius vector Er which becomes smaller than the radius vector r. In a case where the radius vector change rate is "1", even assuming that the processing for changing the radius vector r is performed, the magnitude of the radius vector r is not changed. In the first processing, the angle θ of the coordinates of the radius vector variation range R1 is not changed.

The radius vector change rate is represented by the inclination of a "straight line L1" indicating the tangent line of a line CV1, which defines the relationship between the radius vector r and the radius vector Er, the inclination of the straight line L1 within a range of "rp" to "rB" is greater than "1", and the inclination of the straight line L1 within a range of "rA" to "rp" is smaller than "1". In contrast, the radius vector r outside the radius vector variation range R1 is converted to the radius vector Er which is equivalent to the radius vector r (identical conversion). The inclination of the straight line L1 outside the radius vector variation range R1 is "1".

Figure 7:
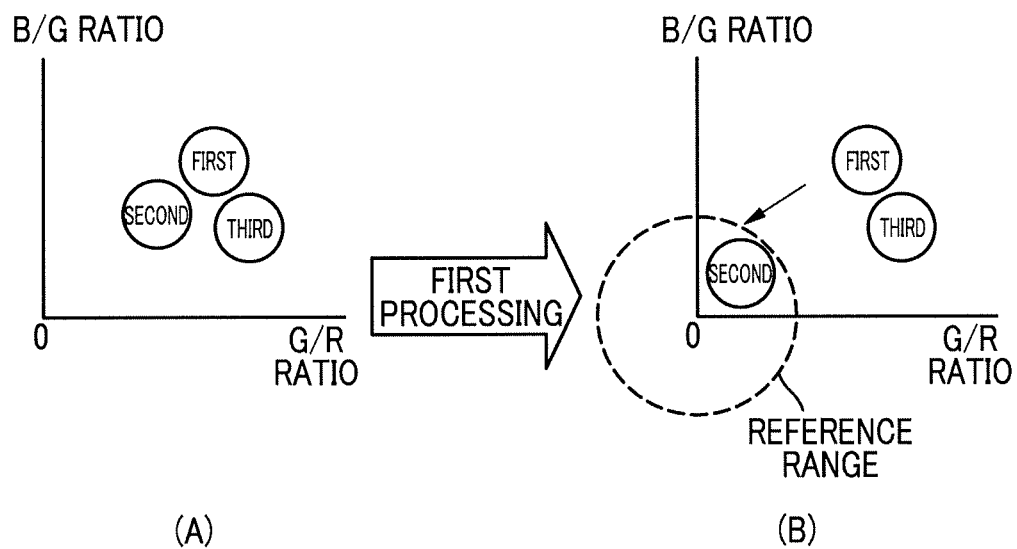
FIG. 7 is an explanatory view showing the operation and the effects of the first processing.

As shown in FIG. 7(A), before the first processing, the first range (in FIG. 7, denoted as "first"), the second range (in FIG. 7, denoted as "second"), and the third range (in FIG. 7, denoted as "third") are close to one another. Meanwhile, after the first processing, as shown in FIG. 7(B), only the coordinates of the second range are moved to a reference range including the origin in a state where the coordinates of the first range and the third range are maintained unmoved. The reference range is a low saturation range not including the first and third ranges after the first processing.

Figure 8A:
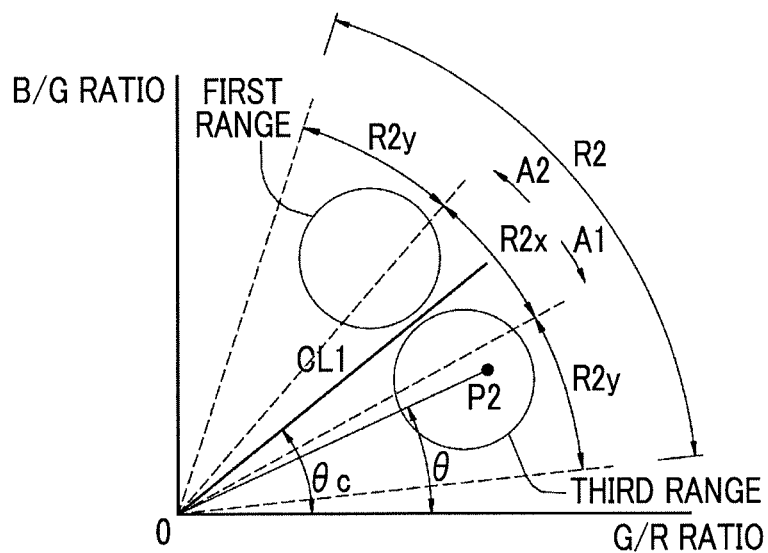
FIG. 8A is an explanatory view showing second processing.

In the second processing, as shown in FIG. 8A, in a feature space formed by the B/G ratio on the vertical axis and the G/R ratio on the horizontal axis, the angle θ of coordinates P2 within the angle variation range R2 is changed, and the angle θ of coordinates outside the angle variation range R2 is not changed. The angle variation range R2 is set so as to include the first range and the third range. In the second processing, the radius vector r of the coordinates of the angle variation range R2 is not changed.

Figure 8B:
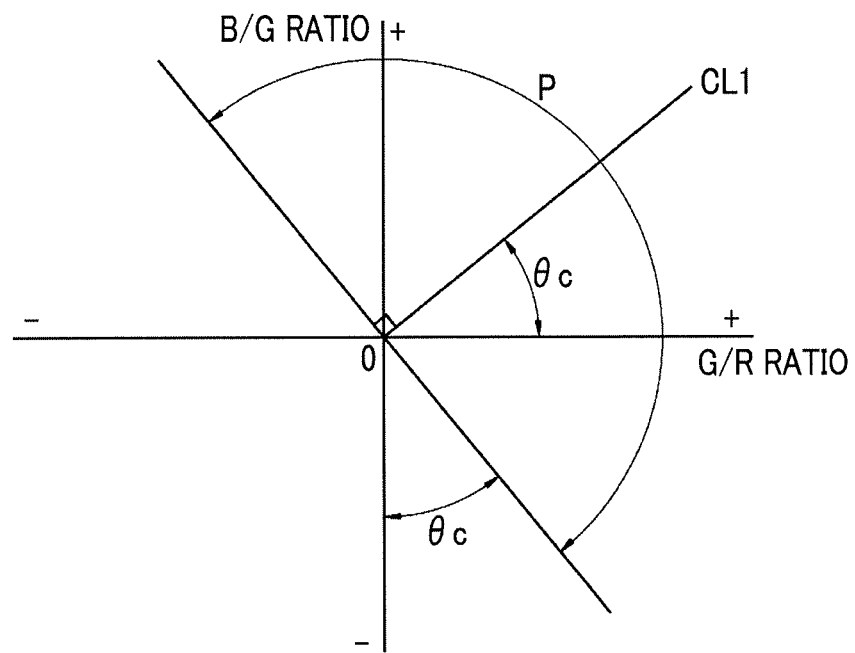
FIG. 8B is a graph showing a range of moment of an angle θ within an angle variation range R2.

In the angle variation range R2, a first center line CL1 is set between the first range and the third range. The first center line CL1 has an angle θc, and in the second processing, rotation in a clockwise direction A1 at an angle θ equal to or less than the angle θc in the angle variation range R2 is performed and rotation in a counterclockwise direction A2 an angle θ equal to or greater than the angle θc in the angle variation range R2 is performed. It is preferable that the coordinates in the angle variation range R2 are moved within a range of +90 degrees from the first center line CL1 (in a case where the "positive" horizontal axis is 0° and the angle is expressed by 0° to 360°, a range P (see FIG. 8B) of "270°+θc" to "θc+900") with the second processing. In a case where an angle change rate is "1", even assuming that the processing for changing the angle θ is performed, the magnitude of the angle θ is not changed.

Figure 9:
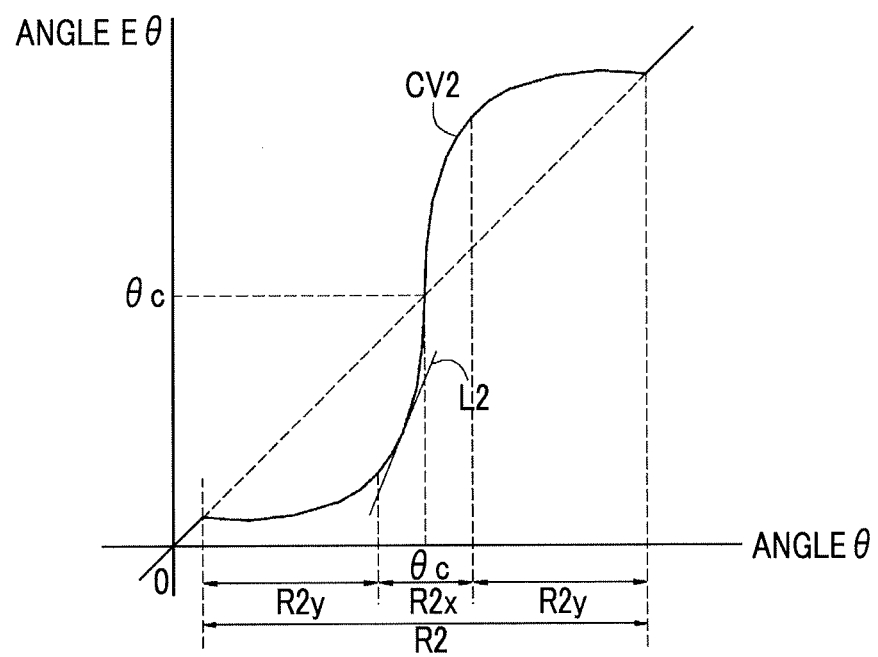
FIG. 9 is a graph showing the relationship between the angle θ and an angle Eθ after the second processing.

With the second processing described above, as shown in FIG. 9, in the angle variation range R2, the angle θ equal to or less than the angle θc is changed to the angle Eθ which becomes smaller than the angle θ, and the angle θ equal to or greater than the angle θc is changed to the angle Eθ which becomes greater than the angle θ. At this time, expansion processing for changing the angle θ in a given range R2x including the first center line CL1 at an angle change rate Wx greater than "1" is performed, and compression processing for changing the angle θ in a range R2y exceeding the range R2x at an angle change rate Wy smaller than "1" is performed.

The angle change rate is represented by the inclination of a "straight line L2" indicating the tangent line of a line CV2, which defines the relationship between the angle θ and the angle Eθ, the inclination of the straight line L2 is greater than "1" within the range R2x, and the inclination of the straight line L2 is smaller than "1" within the range R2y. In contrast, the angle θ outside the angle variation range R2 is converted to the angle Eθ which is equivalent to the angle θ (identical conversion).

The inclination of the straight line L2 outside the angle variation range R2 is "1".

Figure 10:
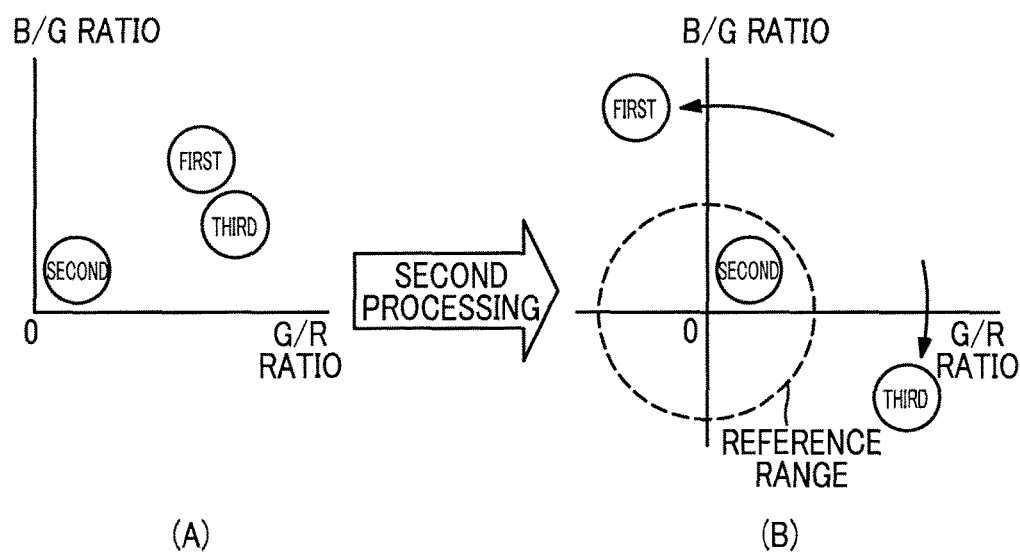
FIG. 10 is an explanatory view showing the operation and the effects of the second processing.

As shown in FIG. 10(A), before the second processing, while the first range (in FIG. 10, denoted as "first") and the third range (in FIG. 10, denoted as "third") are distant from the second range (in FIG. 10, denoted as "second"), the first range and the third range are close to each other. After the second processing, as shown in FIG. 10(B), the coordinates of the second range are maintained in the reference range, most of the coordinates of the first range are moved to the second quadrant of the feature space, and most of the coordinates of the third range are moved to the fourth quadrant of the feature space. With this, the coordinates of the first range, the second range, and the third range are completely distant from each other. In the first special image obtained after the second processing, the boundary between an atrophic part where there is an atrophic mucosa or a deep blood vessel or the like which becomes see-through due to atrophy below the atrophic mucosa, and a normal part where there is a normal mucosa is clarified and displayed.

The second special image processing unit 64b comprises the same configuration as the first special image processing unit 64a. In the second special image processing unit 64b, processing in the angle expansion/compression unit 75 is different from the second processing in the first special image processing unit 64a. Other than that, the same processing is performed. A "second moving processing unit" of the invention corresponds to a configuration including the radius vector expansion/compression unit 74 and the angle expansion/compression unit 75 in the second special image processing unit 64b.

Figure 11A:
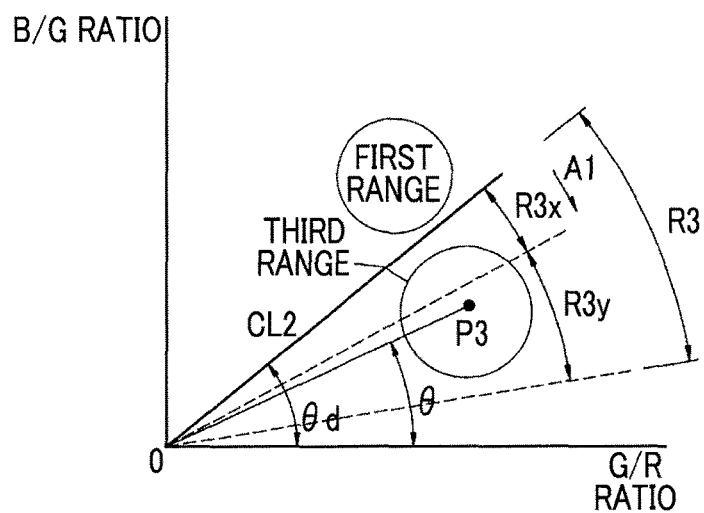
FIG. 11A is an explanatory view showing third processing.

The angle expansion/compression unit 75 of the second special image processing unit 64b performs third processing for moving the coordinates of the third range based on the radius vector r and the angle θ after the first processing by changing the angle θ in a state where the coordinates of the first range are maintained. In the third processing, as shown in FIG. 11A, in a feature space formed by the B/G ratio on the vertical axis and the G/R ratio on the horizontal axis, the angle θ of coordinates P3 within an angle variation range R3 is changed, and the angle θ of coordinates outside the angle variation range R3 is not changed. The angle variation range R3 is set so as to include the third range but not to include the first range. In the third processing, the radius vector r of the coordinates of the angle variation range R3 is not changed.

Figure 11B:
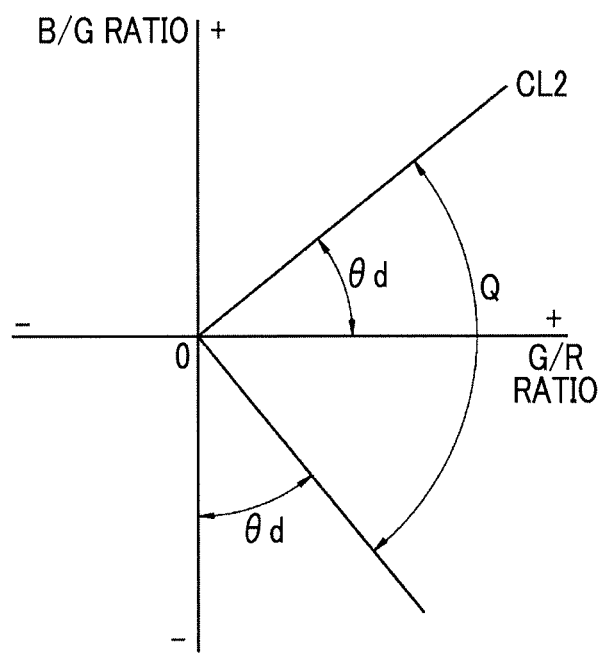
FIG. 11B is a graph showing a moving range of an angle θ within an angle variation range R3.

In the angle variation range R3, a second center line CL2 is set between the first range and the third range. The second center line CL2 has an angle θd, and in the angle variation range R3, rotation in a clockwise direction A1 at an angle θ equal to or less than the angle θd is performed. It is preferable that the coordinates of the angle variation range R3 are moved to a range of −90 degrees from the second center line CL2 (in the feature space, in a case where the "positive" horizontal axis is 0° and the angle is expressed by 0° to 360°, a range Q (see FIG. 11B) of "270°+θd" to "θd") with the third processing. In a case where the angle change rate is "1", even assuming that the processing for changing the angle θ is performed, the magnitude of the angle θ is not changed.

Figure 12:
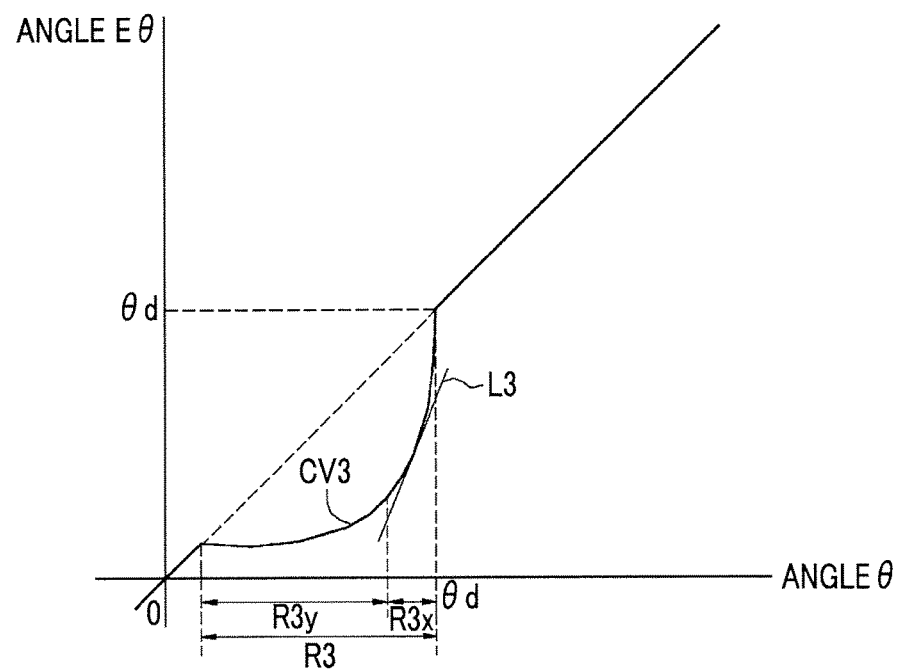
FIG. 12 is a graph showing the relationship between the angle θ and an angle Eθ after the third processing.

With the third processing described above, as shown in FIG. 12, the angle θ is changed to the angle Eθ equal to or less than the angle θ within the angle variation range R3. At this time, expansion processing for changing the angle θ of a given range R3x including the second center line CL2 at an angle change rate Wx greater than "1" is performed, and compression processing for changing the angle θ in a range R3y exceeding the range R3x at an angle change rate Wy smaller than "1" is performed.

The angle change rate is expressed by the inclination of a "straight line L3" indicating the tangent line of a line CV3, which defines the relationship between the angle θ and the angle Eθ, the inclination of the straight line L3 within the range R3x is greater than "1", and the inclination of the straight line L3 within the range R3y is smaller than "1". In contrast, the angle θ outside the angle variation range R3 is converted to the angle Eθ which is equivalent to the angle θ (identical conversion). The inclination of the straight line L3 outside the angle variation range R3 is "1".

Figure 13:
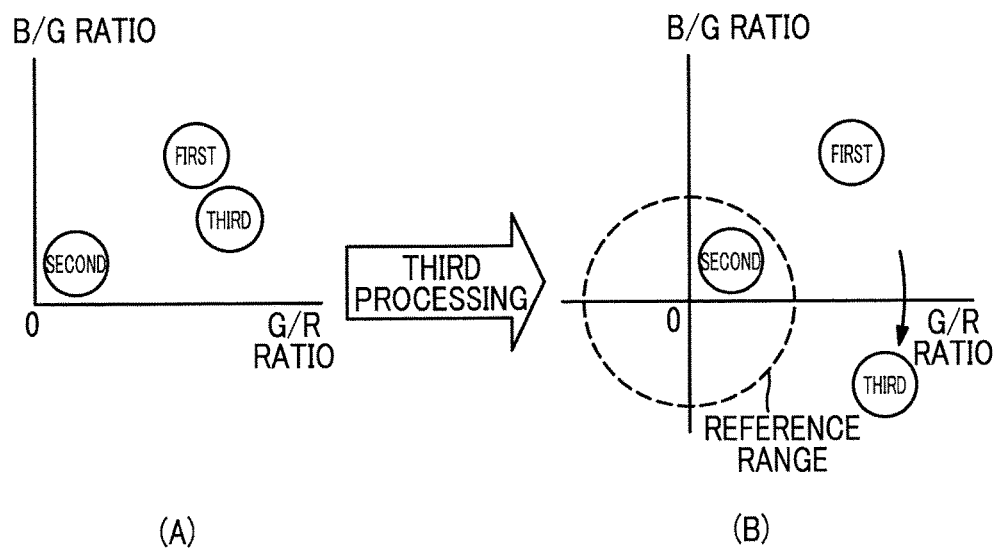
FIG. 13 is an explanatory view showing the operation and the effects of the third processing.

As shown in FIG. 13(A), before the third processing, while the first range (in FIG. 13, denoted as "first") and the third range (in FIG. 13, denoted as "third") are distant from the second range (in FIG. 13, denoted as "second"), the first range and the third range are close to each other. After the third processing, as shown in FIG. 13(B), most of the coordinates of the third range are moved to the fourth quadrant of the feature space while maintaining the coordinates of the second range in the reference range in a state where the coordinates of the first range are maintained unchanged. Moving the coordinates of the third range from the first quadrant to the fourth quadrant corresponds to changing the hue on the second special image while maintaining saturation. With this, the coordinates of the first range, the second range, and the third range are completely distant from each other.

In the second special image obtained after the third processing, a normal part is displayed while maintaining the color, and an atrophic mucosa in an atrophic part where atrophic gastritis occurs is displayed in a faded color. On the second special image, it is possible to clearly display a deep blood vessel which becomes see-through below the atrophic mucosa due to atrophy by changing the color from red to a color, such as magenta. Accordingly, since the second special image is displayed in an original color in the event that atrophic gastritis occurs, the difference in color between the normal part and the atrophic part is made distinct.

Figure 14:
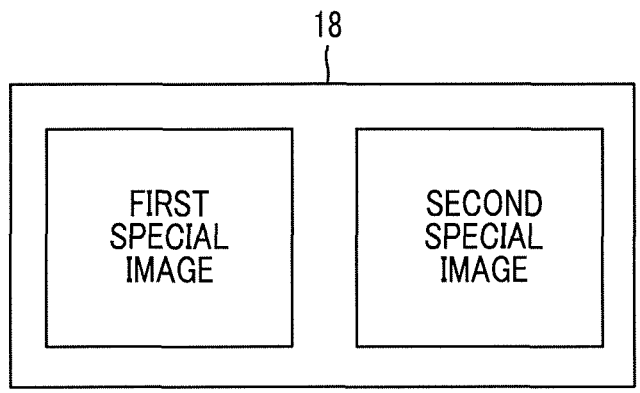
FIG. 14 is an image diagram of a monitor on which a first special image and a second special image are displayed simultaneously.

The simultaneous display image processing unit 64c generates a special image for simultaneous display based on the first special image and the second special image generated by the first special image processing unit 64a and the second special image processing unit 64b. As shown in FIG. 14, the monitor 18 displays the first special image on one side and the second special image on the other side based on the special image for simultaneous display. The first special image is an image which facilitates the recognition of the position or the like of the atrophic part since the boundary between the normal part and the atrophic part is extremely clear, but is an image which gives the doctor a sense of discomfort since the normal part is displayed in a pseudo color which is not the original color of the gastric mucosa. In the event of comparing with the first special image, the second special image is an image which does not give the doctor a sense of discomfort wince the boundary between the normal part and the atrophic part is clear to a certain level and the normal part is displayed in the original color of the stomach. It is possible to detect the boundary between the normal part and the atrophic part while recognizing the color of the normal part by displaying the two images of the first special image and the second special image simultaneously.

Figure 15:
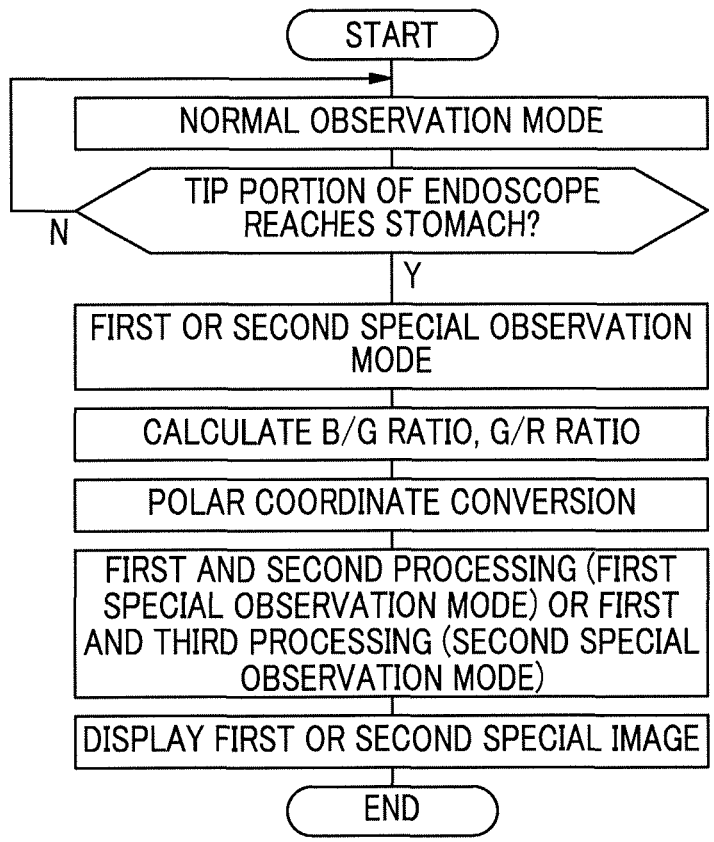
FIG. 15 is a flowchart showing a sequence of flow of the invention.

Next, a sequence of flow of the invention will be described along the flowchart of FIG. 15. First, the observation mode is set to the normal observation mode, and the insertion portion 12a of the endoscope 12 is inserted into the specimen. After the tip portion 12d of the insertion portion 12a reaches the stomach, the mode selection SW 13a is operated to switch the observation mode from the normal observation mode to the first or second special observation mode. In a case of diagnosing atrophic gastritis while observing both of the first special image and the second special image, the observation mode is switched to the simultaneous observation mode.

The B/G ratio and the G/R ratio are calculated by the signal ratio calculation unit 72 based on the RGB image signals obtained after the observation mode is switched to the first or second special observation mode. Next, the calculated B/G ratio and G/R ratio are converted to the radius vector r and the angle θ by polar coordinate conversion.

Next, in a case where the observation mode is set to the first special observation mode, in the feature space formed by the B/G ratio and the G/R ratio, the first processing is performed for moving the second range, in which the atrophic mucosa atrophied due to atrophic gastritis is distributed, to the reference range in a state where the coordinates of the first range in which the normal mucosa is distributed and the coordinates of the third range which is below the atrophic mucosa atrophied due to atrophic gastritis and in which a deep blood vessel which becomes see-through along with atrophy is distributed are maintained. After the first processing, the second processing for moving the coordinates of the first range and the coordinates of the third range so as to be distant from each other is performed. The first special image is generated based on the B/G ratio and the G/R ratio after the first processing and the second processing. The first special image is displayed on the monitor 18.

In a case where the observation mode is set to the second special observation mode, in the feature space formed by the B/G ratio and the G/R ratio, the same first processing as described above is performed. After the first processing, the third processing for moving the coordinates of the third range in a state where the coordinates of the first range are maintained is performed. The second special image is generated based on the B/G ratio and the G/R ratio after the first processing and the third processing. The second special image is displayed on the monitor 18.

The simultaneous observation mode is not limited to a case where the first special image and the second special image are displayed simultaneously, and for example, simultaneous display of the first special image and the normal image may be displayed simultaneously. The second special image and the normal image may be displayed simultaneously. In this case, display images are generated by the normal image processing unit 62 and the special image processing unit 64, pass through the video signal generation unit 66, and are displayed on the monitor 18 through the video signal generation unit 66.

In the simultaneous observation mode, the first special image and a third special image which is not subjected to any of the first to third processing may be displayed simultaneously. The third special image is generated by a third special image processing unit (not shown) provided in the special image processing unit 64. In this case, the third special image processing unit does not comprise the polar coordinate conversion unit 73, the radius vector expansion/compression unit 74, the angle expansion/compression unit 75, the Cartesian coordinate conversion unit 76, and the RGB conversion unit 77 necessary for the first to third processing, unlike the first and second special image processing units 64a and 64b. Other than that, the components are the same as those of the first and second special image processing units 64a and 64b. In the event of generating the third special image, it is preferable to emit light of each color while making the light intensity of violet light V larger than the light intensity of blue light B, green light G, and red light R. The third special image obtained under the light emission condition is an image which is displayed with a superficial blood vessel enhanced in a state where the entire image is maintained in a bright state.

Second Embodiment

In a second embodiment, an observation target is illuminated using a laser beam source and a phosphor, instead of the LEDs 20a to 20d of the four colors shown in the first embodiment. Other than that, the components are the same as those in the first embodiment.

Figure 16:
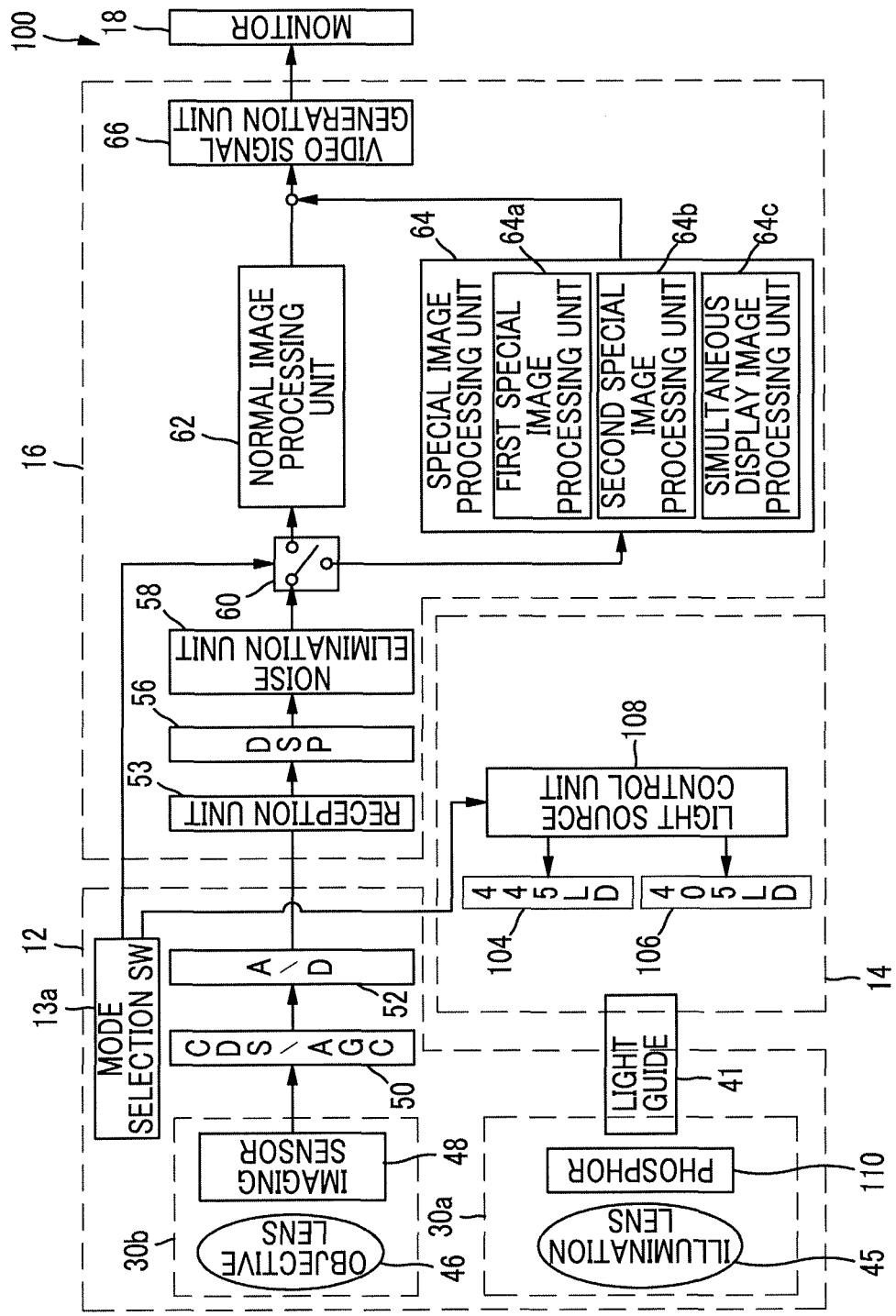
FIG. 16 is a block diagram showing functions of an endoscope system of a second embodiment.

As shown in FIG. 16, in an endoscope system 100 of the second embodiment, a light source device 14 is provided with, instead of the LEDs 20a to 20d of the four colors, a blue laser beam source (in FIG. 16, denoted as "445LD") 104 which emits a blue laser beam having a center wavelength of 445±10 nm, and a blue-violet laser beam source (in FIG. 16, denoted as "405LD") 106 which emits a blue-violet laser beam having a center wavelength of 405±10 nm. Light emission from semiconductor light emitting elements of the light sources 104 and 106 is individually controlled by a light source control unit 108, and the light quantity ratio between emitted light from the blue laser beam source 104 and emitted light of the blue-violet laser beam source 106 is freely changeable.

The light source control unit 108 drives the blue laser beam source 104 in a case of the normal observation mode. In contrast, in the first or second special observation mode or the simultaneous observation mode, both of the blue laser beam source 104 and the blue-violet laser beam source 106 are driven, and the light emission intensity of the blue laser beam is controlled so as to be greater than the light emission intensity of the blue-violet laser beam. The laser beams emitted from the light sources 104 and 106 are incident on the light guide 41 through optical members (all not shown), such as a condenser lens, an optical fiber, and a multiplexer.

It is preferable that the half width of the blue laser beam or the blue-violet laser beam is about ±10 nm. For the blue laser beam source 104 and the blue-violet laser beam source 106, a broad-area type InGaN-based laser diode may be used, or an InGaNAs-based laser diode or a GaNAs-based laser diode may be used. As the light sources described above, a light emitting element, such as a light emitting diode, may be used.

The illumination optical system 30a is provided with a phosphor 110 on which the blue laser beam or the blue-violet laser beam from the light guide 41 is incident, in addition to the illumination lens 45. The phosphor 110 is irradiated with the blue laser beam, whereby fluorescence is emitted from the phosphor 110. A part of the blue laser beams is transmitted through the phosphor 110. The blue-violet laser beam is transmitted through the phosphor 110 without exciting the phosphor 110. The inside of the specimen is irradiated with light emitted from the phosphor 110 through the illumination lens 45.

Figure 17:
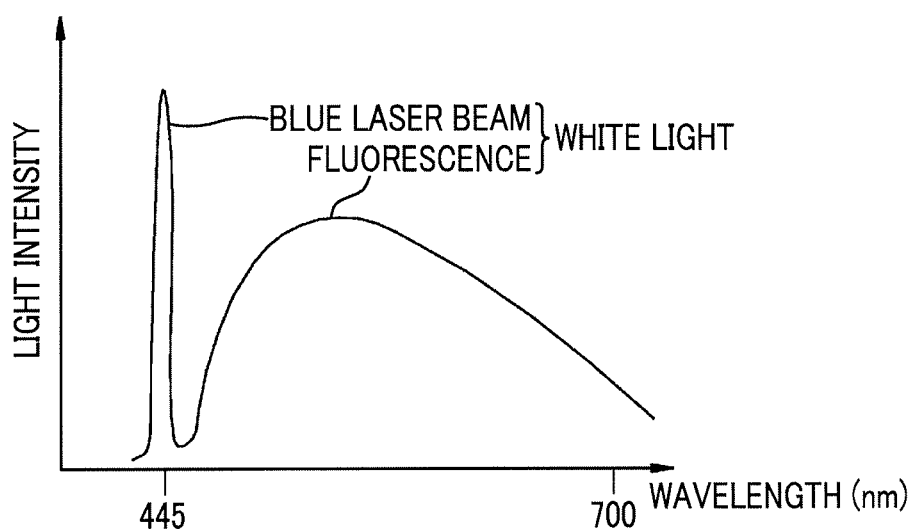
FIG. 17 is a graph showing a light emission spectrum of white light.
Figure 18:
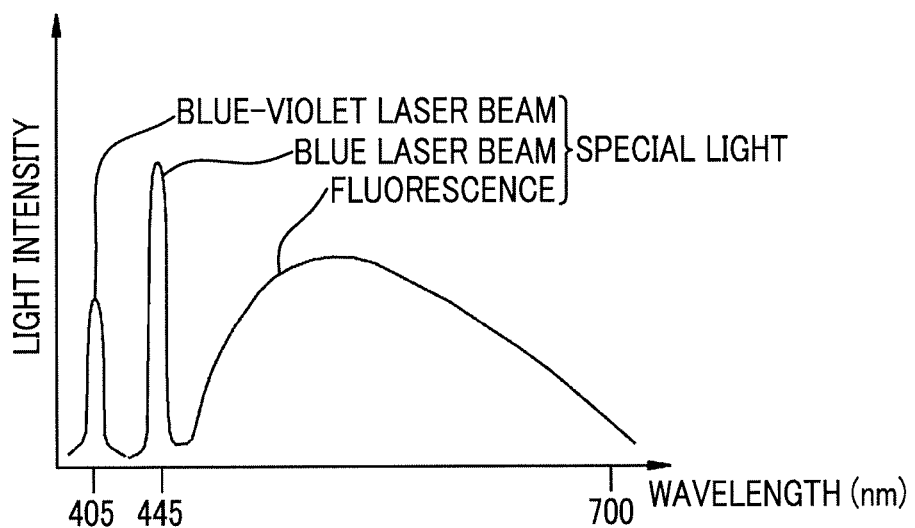
FIG. 18 is a graph showing a light emission spectrum of special light.

In the normal observation mode, since the blue laser beam is mostly incident on the phosphor 110, the observation target is irradiated with white light which is the combination of the blue laser beam and and the fluorescence emitted from the phosphor 110 excited by the blue laser beam as shown in FIG. 17. In the first or second special observation mode or the simultaneous observation mode, since both of the blue-violet laser beam and the blue laser beam are incident on the phosphor 110, the inside of the specimen is irradiated with special light which is the combination of the blue-violet laser beam, the blue laser beam, and the fluorescence emitted from the phosphor 110 excited by the blue laser beam as shown in FIG. 18.

It is preferable that the phosphor 110 includes a plurality of phosphors (for example, phosphors, such as YAG-based phosphors or $BaMgAl_{10}O_{17}$ (BAM)) which absorb a part of the blue laser beams and is excited to emit green to yellow colors. As in this configuration example, assuming that a semiconductor light emitting element is used as the excitation light source of the phosphor 110, white light with high intensity is obtained with high light emission efficiency, and it is possible to easily adjust the intensity of white light and to minimize changes in color temperature and chromaticity of white light.

Third Embodiment

In a third embodiment, an observation target is illuminated using a broadband light source, such as a Xenon lamp, and a rotary filter, instead of the LEDs 20a to 20d of the four colors shown in the first embodiment. The observation target is imaged with a monochrome imaging sensor, instead of the color imaging sensor 48. Other than that, the components are the same as those in the first embodiment.

Figure 19:
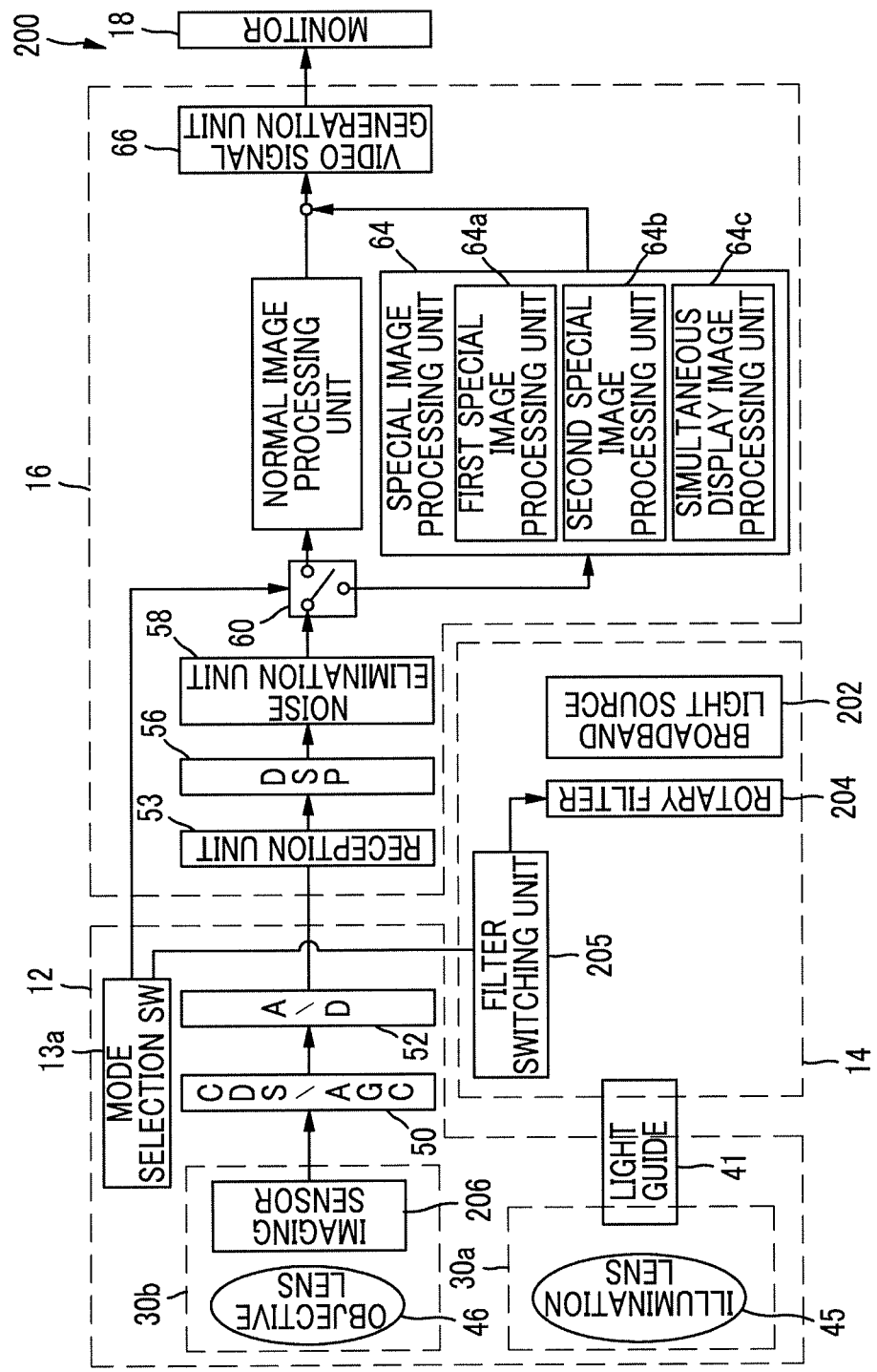
FIG. 19 is a block diagram showing functions of an endoscope system of a third embodiment.

As shown in FIG. 19, a light source device 14 of an endoscope system 200 of the third embodiment is provided with a broadband light source 202, a rotary filter 204, and a filter switching unit 205, instead of the LEDs 20a to 20d of the four colors. The imaging optical system 30b is provided with a monochrome imaging sensor 206 with no color filters, instead of the color imaging sensor 48.

The broadband light source 202 is a Xenon lamp, a white LED, or the like, and emits white light having a wavelength band from blue to red. The rotary filter 204 comprises an internal filter 208 for a normal observation mode and an external filter 209 for a special observation mode (see FIG. 20). The filter switching unit 205 moves the rotary filter 204 in a radius direction, inserts the filter 208 for a normal observation mode of the rotary filter 204 into the optical path of white light in the event that the normal observation mode is set by the mode selection SW 13a, and inserts the filter 209 for a special observation mode of the rotary filter 204 into the optical path of white light in the event that the first or second special observation mode is set.

Figure 20:
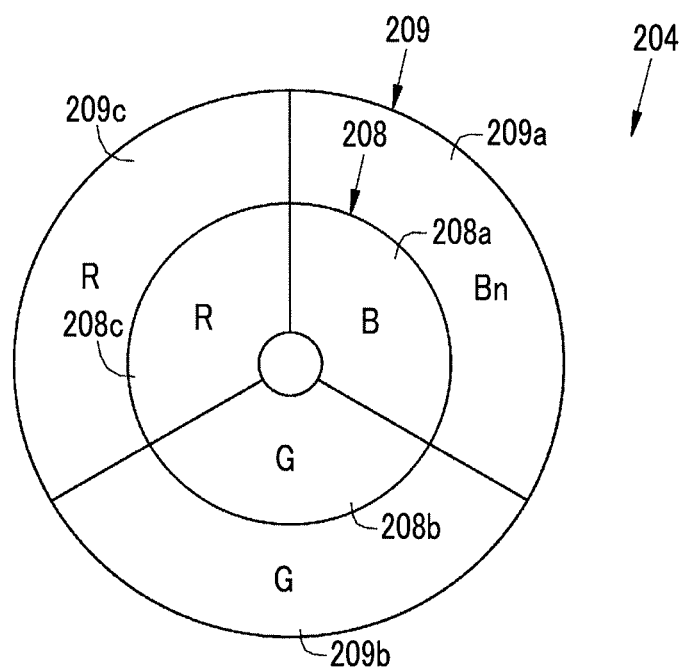
FIG. 20 is a plan view showing a rotary filter.

As shown in FIG. 20, the filter 208 for a normal observation mode is provided with, in a circumferential direction, a B filter 208a which transmits blue light from white light, a G filter 208b which transmits green light from white light, and an R filter 208c which transmits red light from white light. Accordingly, in the normal observation mode, the rotary filter 204 rotates, whereby the observation target is alternately irradiated with blue light, green light, and red light.

The filter 209 for a special observation mode is provided with, in a circumferential direction, a Bn filter 209a which transmits blue narrowband light having a specific wavelength from white light, a G filter 209b which transmits green light from white light, and an R filter 209c which transmits red light from white light. Accordingly, in the special observation mode, the rotary filter 204 rotates, whereby the observation target is alternately irradiated with blue narrowband light, green light, and red light.

In the endoscope system 200, in the normal observation mode, the inside of the specimen is imaged by the monochrome imaging sensor 206 each time the observation target is irradiated with blue light, green light, and red light. With this, image signals of three colors of RGB are obtained. A normal image is generated based on the image signals of RGB by the same method as in the foregoing first embodiment.

In the first or second special observation mode or the simultaneous observation mode, the inside of the specimen is imaged by the monochrome imaging sensor 206 each time the observation target is irradiated with blue narrowband light, green light, and red light. With this, a Bn image signal, a G image signal, and an R image signal are obtained. A first or second special image is generated based on the Bn image signal, the G image signal, and the R image signal. In generating the first or second special image, the Bn image signal is used, instead of the B image signal. Except for this, the generation of the first or second special image is performed by the same method as in the first embodiment.

Fourth Embodiment

In a fourth embodiment, RGB image signals necessary for generating a normal image or a first or second special image is acquired using a swallow-type capsule endoscope, instead of the insertion-type endoscope 12 and the light source device 14.

Figure 21:
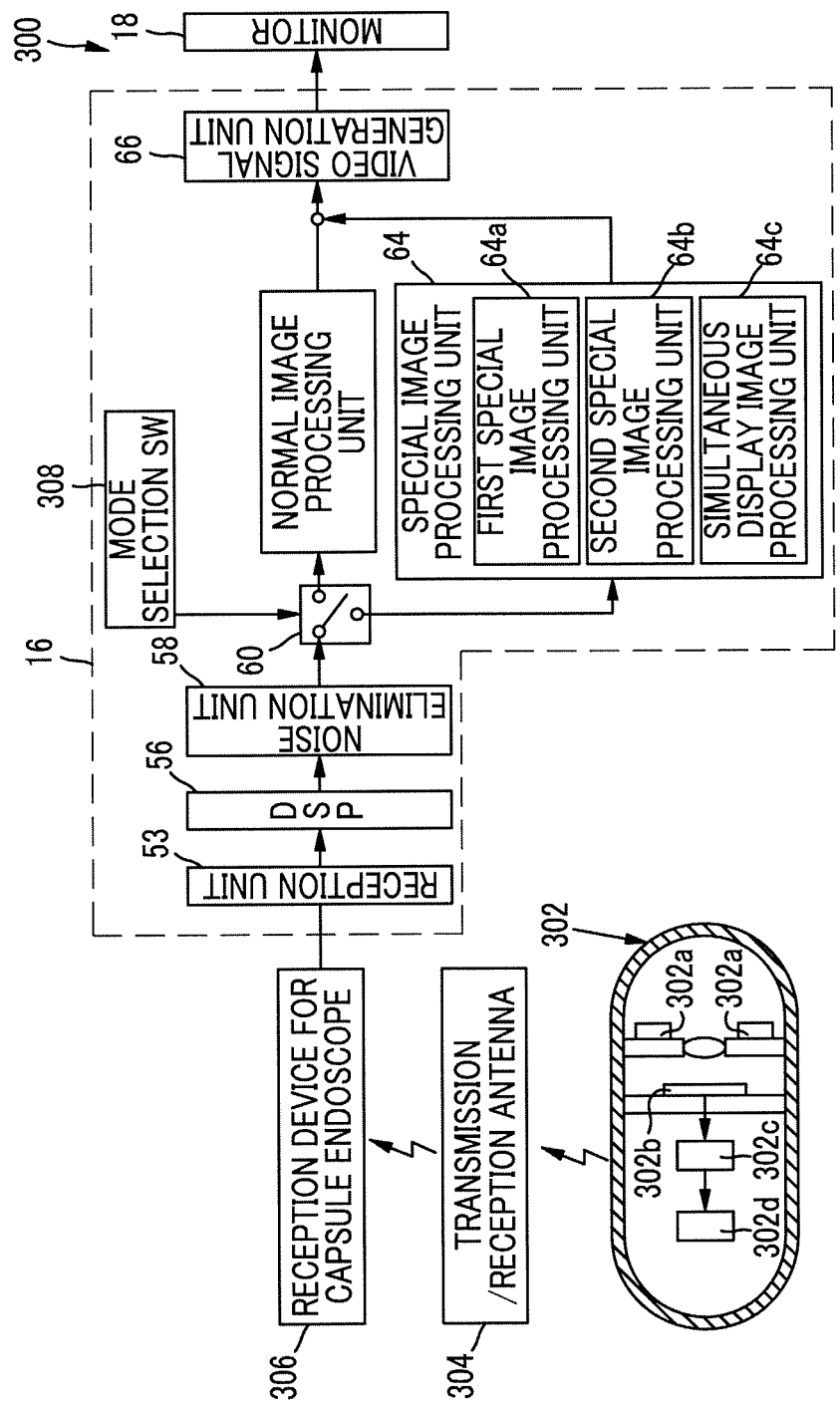
FIG. 21 is a diagram showing functions of a capsule endoscope system of a fourth embodiment.

As shown in FIG. 21, a capsule endoscope system 300 of the fourth embodiment comprises a capsule endoscope 302, a transmission/reception antenna 304, a reception device 306 for a capsule endoscope, the processor device 16, and the monitor 18. The capsule endoscope 302 comprises an LED 302a, an imaging sensor 302b, an image processing unit 302c, and a transmission antenna 302d. While the processor device 16 is the same as that in the first embodiment, in the fourth embodiment, a mode selection SW 308 for switching among the normal observation mode, the first special observation mode, and the second special observation mode is newly provided.

A plurality of LEDs 302a which emit white light are provided in the capsule endoscope 302. As the LEDs 302a, it is preferable to use a white LED or the like comprising a blue light source and a phosphor which performs wavelength of light from the blue light source to emit fluorescence. A laser diode (LD) may be used, instead of the LED. The observation target is illuminated with white light emitted from the LEDs 302a.

The imaging sensor 302b is a color imaging sensor, images the observation target illuminated with white light, and outputs RGB image signals. As the imaging sensor 302b, it is preferable to use a charge coupled device (CCD) imaging sensor or a complementary metal-oxide semiconductor (CMOS) imaging sensor. The RGB image signals output from the imaging sensor 302b are subjected to processing for converting the RGB image signals to signals to be transmitted through the transmission antenna 302d in the image processing unit 302c. The RGB image signals having passed through the image processing unit 302c are transmitted from the transmission antenna 302d to the transmission/reception antenna 304 in a wireless manner.

The transmission/reception antenna 304 is affixed to the subject's body, and receives the RGB image signals from the transmission antenna 302d. The transmission/reception antenna 304 transmits the received RGB image signals to the reception device 306 for a capsule endoscope in a wireless manner. The reception device 306 for a capsule endoscope is connected to the reception unit 53 of the processor device 16, and transmits the RGB image signals from the transmission/reception antenna 304 to the reception unit 53.

Figure 22:
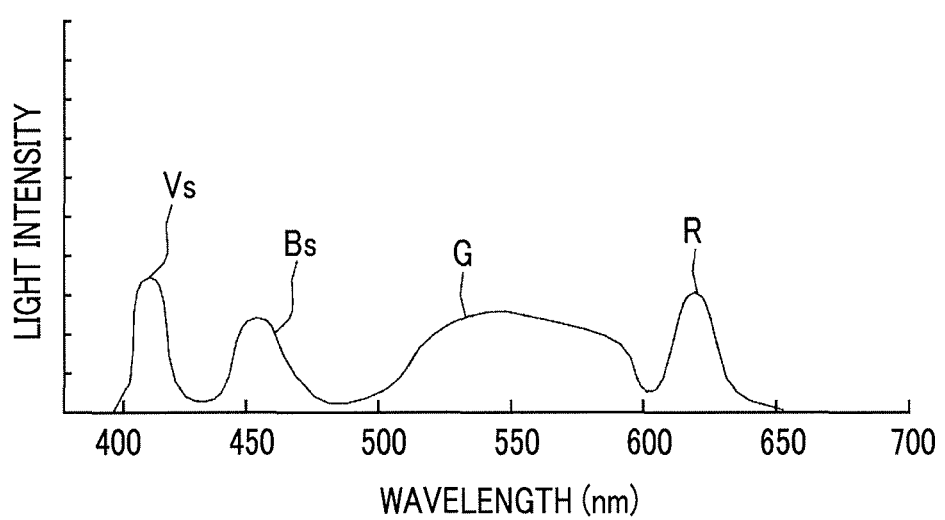
FIG. 22 is a graph showing light emission spectra of violet light V, blue light B, green light G, and red light R different from those of FIG. 3.

In the foregoing embodiments, although light of the four colors having the light emission spectra shown in FIG. 3 is used, the light emission spectra is not limited thereto. For example, as shown in FIG. 22, green light G and red light R may have the same spectra as those shown in FIG. 3, and violet light Vs may be light having a center wavelength of 410 nm to 420 nm and a wavelength range slightly shifted to a longer wavelength side than violet light V of FIG. 3. Blue light Bs may be light having a center wavelength of 445 nm to 460 nm and a wavelength range slightly shifted to a shorter wavelength side than blue light B of FIG. 3.

Figure 23:
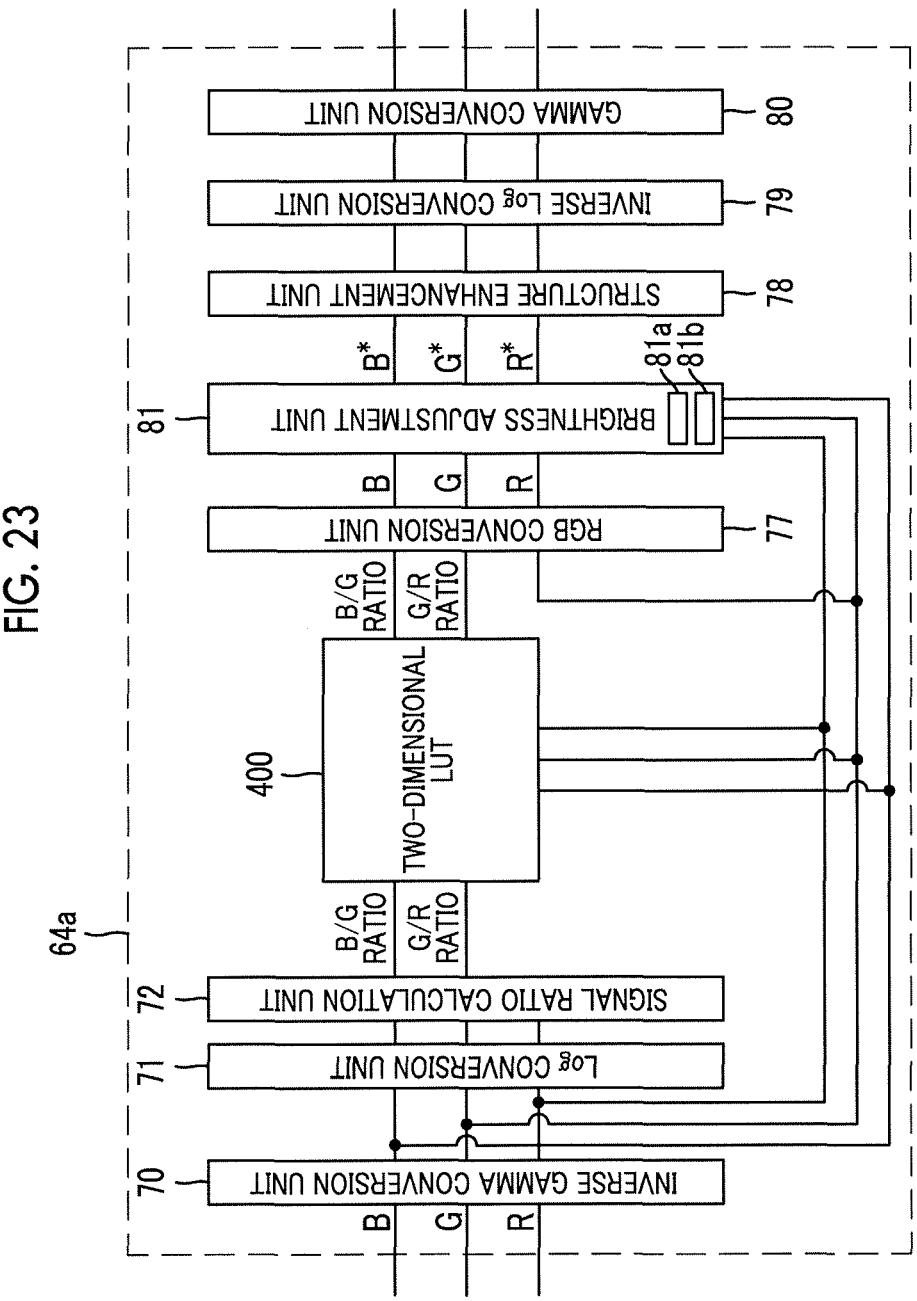
FIG. 23 is a block diagram showing functions of a first or second special image processing unit in a case of using a two-dimensional LUT.

In the foregoing embodiments, although the B/G ratio and the G/R ratio are converted to the radius vector r and the angle θ by polar coordinate conversion, the first and second processing or the first processing and the third processing are performed based on the radius vector r and the angle θ after conversion, and thereafter, the radius vector r and the angle θ are returned to the B/G ratio and the G/R ratio again, as shown in FIG. 23, the B/G ratio and the G/R ratio may be converted directly to the B/G ratio and the G/R ratio after the first and second processing or the first and third processing using a two-dimensional LUT 400 without performing polar coordinate conversion or the like.

In the two-dimensional LUT 400, the B/G ratio and the G/R ratio are stored in relation to the B/G ratio and the G/R ratio subjected to the first and second processing (or subjected to the first processing and the third processing) obtained by performing the first and second processing (or the first processing and the third processing) based on the B/G ratio and the G/R ratio. The first RGB image signals output from the inverse gamma conversion unit 70 are input to the two-dimensional LUT 400. Alternatively, as in the foregoing embodiments, the first RGB image signals may be input to the RGB conversion unit 77.

In the foregoing embodiments, although the first range and the third range are distant from each other by changing the angle θ through the second processing, the first range and the third range may be distant from each other by other methods. For example, the first range and the third range may be distant from each other by changing the radius vector r, or the first range and the third range may be distant from each other by changing both of the radius vector r and the angle θ. The third processing may be performed for moving the coordinates of the first range while maintaining the coordinates of the third range.

In the foregoing embodiments, although the B/G ratio and the G/R ratio are determined from the first RGB image signals and the feature space is formed by the determined B/G ratio and G/R ratio, in a case where the first B image signal is a narrowband signal which is obtained from narrowband light (for example, light having a half width within a range of 20 nm) with a narrow wavelength range, the difference between the first range and the second range in the feature space and the difference between the first range and the third range are great compared to a case where the first B image signal is a broadband signal which is obtained from broadband light (for example, light having a half width exceeding a range of 20 nm) with a broad wavelength range. As narrowband light, "violet light V" and "blue light B" of the first embodiment are included, the "blue laser beam" or the "blue-violet laser beam" of the second embodiment is included, "blue narrowband light" of the third embodiment is included, and "light of the blue light source" of the fourth embodiment is included.

Figure 24:
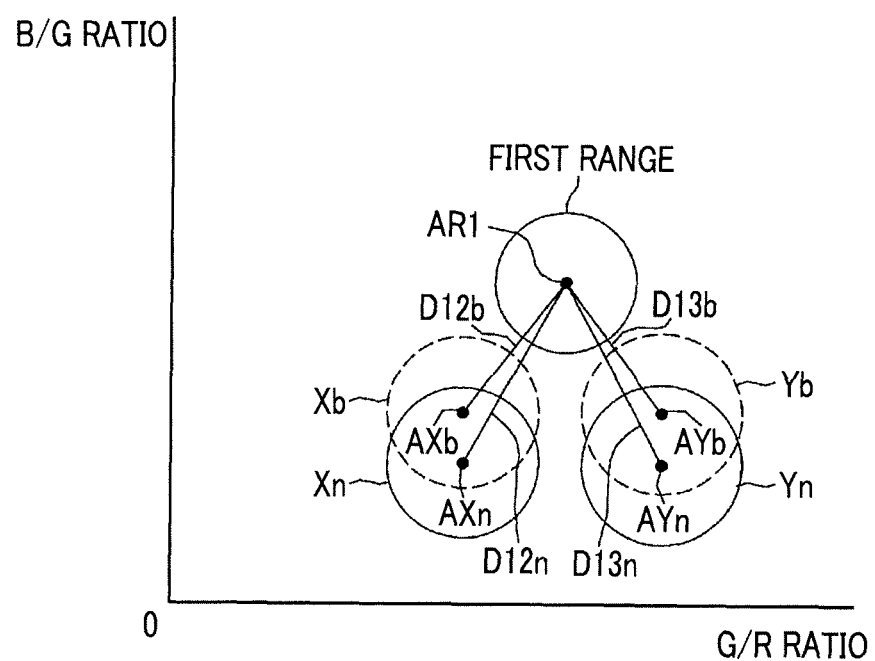
FIG. 24 is an explanatory view showing the positions of a second range and a third range in a feature space in a case where a first B image signal is a narrowband signal and the positions of the second range and the third range in the feature space in a case where the first B image signal is a broadband signal.

In FIG. 24, "Xn" indicates the second range in a case where the first B image signal is a narrowband signal, and "Xb" indicates the second range in a case where the first B image signal is a broadband signal. In the event of comparing "Xn" and "Xb", "Xn" is positioned below "Xb" in the feature space. Furthermore, "Yn" indicates the third range in a case where the first B image signal is a narrowband signal, and "Yb" indicates the third range in a case where the first B image signal is a broadband signal. In the event of comparing "Yn" and "Yb", "Yn" is positioned below "Yb" in the feature space.

As shown in FIG. 24, the difference D12n between an average value AXn of "Xn" and an average value AR1 of the first range is greater than the difference D12b between an average value AXb of "Xb" and the average value AR1 of the first range, and the difference D13n between an average value AYn of "Yn" and the average value AR1 of the first range is greater than the difference D13b between an average value AXb of "Yb" and the average value AR1 of the first range. As described above, in a case where the first B image signal is a narrowband signal, the differences between the first range and the second and third ranges are already large before performing processing for expanding or compressing the differences. The processing for expanding or compressing the first to third ranges in this state is performed, whereby it is possible to more clearly the difference between the normal part and the atrophic part.

Assuming that the first G image signal is a narrowband signal, similarly to the above, it is possible to make the difference between the first range and the second range and the difference between the first range and the third range large compared to a case where the first G image signal is a broadband signal. In addition, the invention is not limited to a case where the first B image signal or the first G image signal is a narrowband signal as described above, and assuming that an image signal of at least one color of the first RGB image signals is a narrowband signal, it is possible to make the difference between the first range and the second range and the difference between the first range and the third range large compared to a case where all of the first RGB image signals are broadband signals. Furthermore, in regard to the narrowband signal, as described above, in addition to the signal obtained from narrowband light, a signal obtained by spectroscopic estimation processing described in JP2003-093336A is also included.

The invention can be applied to various medical image processing devices, in addition to the endoscope systems described in the first to third embodiments or the processor device incorporated in the capsule endoscope system described in the fourth embodiment.

EXPLANATION OF REFERENCES 10, 100, 200: endoscope system
16: processor device (medical image processing device)
72: signal ratio calculation unit
64a: first special image processing unit
64b: second special image processing unit
74: radius vector expansion/compression unit
75: angle expansion/compression unit
77: RGB conversion unit (color image signal conversion unit)
81: brightness adjustment unit

What is claimed is:
1. A medical image processing device comprising:
a processing circuitry configured for:
performing input processing of a first color image signal, at least an image signal of one color in the first color image signal is a narrowband signal obtained from narrowband light having a half width within a range of 20 nm;
calculating a first signal ratio between image signals of two colors in the first color image signal and a second signal ratio between image signals of two colors different from those in the first signal ratio; and
performing, in a feature space formed by the first signal ratio and the second signal ratio, moving processing for moving a first range, a second range, and a third range where an observation target in a subject is distributed, in order to make the first range, the second range, and the third range distant from each other; and
a display unit which displays a special image obtained from the first signal ratio and the second signal ratio after the moving processing, the color difference among the first range, the second range, and the third range in the special image is greater than a color difference between the first range, the second range, and the third range in a special image obtained in a case where image signals of all colors of the first color image signal are broadband signals.

2. The medical image processing device according to claim 1,
wherein the moving processing includes a first processing and a second processing, the first processing being performed for moving the coordinates of the second range to a reference range determined in the feature space, and the second processing being performed for moving at least one of the coordinates of the first range and the coordinates of the third range without moving the second range.

3. The medical image processing device according to claim 1,
wherein the moving processing includes a first processing and a third processing, the first processing being performed for moving the coordinates of the second range to a reference range determined in the feature space, and the third processing being performed for moving the third range in a state where the coordinates of the first range are maintained.

4. A medical image processing device comprising: a processing circuitry configured for: performing input processing of a first color image signal, wherein at least an image signal of one color in the first color image signal is a narrowband signal obtained from narrowband light having a half width within a range of 20 nm; calculating a first signal ratio between image signals of two colors in the first color image signal and a second signal ratio between image signals of two colors different from those in the first signal ratio; and performing, in a feature space formed by the first signal ratio and the second signal ratio, moving processing for moving a first range, a second range, and a third range where an observation target in a subject is distributed, in order to make the first range, the second range, and the third range distant from each other; and a display unit which displays a special image obtained from the first signal ratio and the second signal ratio after the moving processing, the color difference among the first range, the second range, and the third range in the special image is greater than a color difference between the first range, the second range, and the third range in a special image obtained in a case where image signals of all colors of the first color image signal are broadband signals, wherein, in the feature space, the difference between the first range and the second range in a case where the image signal of at least one color of the first color image signal is a narrowband signal is greater than the difference between the first range and the second range in a case where the image signals of all colors of the first color image signal are broadband signals, or the difference between the first range and the third range in a case where the image signal of at least one color of the first color image signal is a narrowband signal is greater than the difference between the first range and the third range in a case where the image signals of all colors of the first color image signal are broadband signals.

5. The medical image processing device according to claim 2,
wherein the first processing is performed for moving the coordinates of the second range to the reference range by changing a radius vector of the coordinates of the second range in the feature space.

6. The medical image processing device according to claim 2,
wherein the second processing is performed for moving the coordinates of the first range and the coordinates of the third range so as to be distant from each other by changing an angle of the coordinates of the first range and an angle of the coordinates of the third range in the feature space.

7. The medical image processing device according to claim 2,
wherein the reference range is a range which includes the origin of the feature space, and does not include the first range and the third range.

8. The medical image processing device according to claim 3,
wherein the third processing is performed for moving the coordinates of the third range such that the hue of a second special image obtained from the first signal ratio and the second signal ratio after the first and third processing is changed.

9. The medical image processing device according to claim 1, wherein the processing circuitry further configured for:
converting the first signal ratio and the second signal ratio after the first and second processing to a second color image signal or converts the first signal ratio and the second signal ratio after the first and third processing to a second color image signal; and
adjusting the pixel values of the second color image signal from first brightness information obtained from the first color image signal and second brightness information obtained from the second color image signal.

10. The medical image processing device according to claim 1,
wherein the first signal ratio correlates with a blood vessel depth and the second signal ratio correlates with a blood volume.

11. The medical image processing device according to claim 1, wherein the first signal ratio is a B/G ratio and the second signal ratio is a G/R ratio.

12. An operation method for a medical image processing device comprising: a step in which a processing circuitry performs input processing of a first color image signal, wherein at least an image signal of one color in the first color image signal is a narrowband signal obtained from narrowband light having a half width within a range of 20 nm; a step in which the processing circuitry calculates a first signal ratio between image signals of two colors in the first color image signal and a second signal ratio between image signals of two colors different from those in the first signal ratio; a step in which the processing circuitry performs, in a feature space formed by the first signal ratio and the second signal ratio, moving processing for moving a first range, a second range, and a third range where an observation target in a subject is distributed, in order to make the first range, the second range, and the third range distant from each other; and a step in which a display unit displays a special image obtained from the first signal ratio and the second signal ratio after the moving processing, the color difference among the first range, the second range, and the third range in the special image is greater than a color difference between the first range, the second range, and the third range in a special image obtained in a case where image signals of all colors of the first color image signal are broadband signals.

13. A method of performing medical image processing, comprising: performing input processing of a first color image signal, wherein at least an image signal of one color in the first color image signal is a narrowband signal obtained from narrowband light having a half width within a range of 20 nm; calculating a first signal ratio between image signals of two colors in the first color image signal and a second signal ratio between image signals of two colors different from those in the first signal ratio; performing, in a feature space formed by the first signal ratio and the second signal ratio, moving processing for moving a first range, a second range, and a third range where an observation target in a subject is distributed, in order to make the first range, the second range, and the third range distant from each other; and displaying a special image obtained from the first signal ratio and the second signal ratio after the moving processing, the color difference among the first range, the second range, and the third range in the special image is greater than a color difference between the first range, the second range, and the third range in a special image obtained in a case where image signals of all colors of the first color image signal are broadband signals, wherein, in the feature space, the difference between the first range and the second range in a case where the image signal of at least one color of the first color image signal is a narrowband signal is greater than the difference between the first range and the second range in a case where the image signals of all colors of the first color image signal are broadband signals, or the difference between the first range and the third range in a case where the image signal of at least one color of the first color image signal is a narrowband signal is greater than the difference between the first range and the third range in a case where the image signals of all colors of the first color image signal are broadband signals.

* * * * *